(12) United States Patent
Hannig et al.

(10) Patent No.: US 10,508,457 B2
(45) Date of Patent: Dec. 17, 2019

(54) PANEL WITH COMPLIMENTARY LOCKING ELEMENTS

(71) Applicant: AKZENTA PANEELE + PROFILE GMBH, Kaisersesch (DE)

(72) Inventors: Hans-Jürgen Hannig, Bergisch Gladbach (DE); Erich Schäfers, Demerath (DE)

(73) Assignee: AKZENTA PANEELE + PROFILE GMBH, Kaisersesch (DE)

( * ) Notice: Subject to any disclaimer, the term of this patent is extended or adjusted under 35 U.S.C. 154(b) by 0 days.

(21) Appl. No.: 15/120,658

(22) PCT Filed: Sep. 30, 2015

(86) PCT No.: PCT/EP2015/072564
§ 371 (c)(1),
(2) Date: Aug. 22, 2016

(87) PCT Pub. No.: WO2016/050848
PCT Pub. Date: Apr. 7, 2016

(65) Prior Publication Data
US 2017/0016235 A1    Jan. 19, 2017

(30) Foreign Application Priority Data

Sep. 30, 2014 (DE) .......... 10 2014 114 250

(51) Int. Cl.
*E04F 15/02* (2006.01)
*E04F 15/10* (2006.01)
(Continued)

(52) U.S. Cl.
CPC .......... *E04F 15/02038* (2013.01); *E04C 2/38* (2013.01); *E04F 13/0894* (2013.01); *E04F 15/102* (2013.01)

(58) Field of Classification Search
CPC ............ E04F 13/0894; E04F 15/02033; E04F 2201/0153; E04F 2201/042
See application file for complete search history.

(56) References Cited

U.S. PATENT DOCUMENTS 1,551,544 A * 9/1925 Crooks .................. E04F 15/04
52/578
2,328,051 A * 8/1943 Bull ..................... E04L 32/7457
403/339
(Continued)

FOREIGN PATENT DOCUMENTS

DE        3538538 A1    5/1987
DE    202008011589 U1   11/2008
(Continued)

OTHER PUBLICATIONS

International Preliminary Report on Patentability, dated Apr. 4, 2017, 6pgs. (English translation).

*Primary Examiner* — Joshua J Michener
*Assistant Examiner* — Charissa Ahmad
(74) *Attorney, Agent, or Firm* — Lucas & Mercanti, LLP; Klaus P. Stoffel

(57) ABSTRACT

A panel having a pair of complementary locking elements at mutually opposite panel edges. The locking elements are positively locking holding profiles with a locking groove and a complementary locking tongue respectively. At least at the edge of one of the holding profiles the panel surface has an edge break portion. The holding profile provided with the edge break portion has an upper contact surface beneath the edge break portion and the complementary holding profile has a complementary upper contact surface arranged substantially parallel thereto. A butt joint is produced by contact of two contact surfaces. The butt joint is inclined relative to the panel surface. One of the contact surfaces is associated with a tongue and is inclined downwardly toward the free (Continued)

end of the tongue in question and the complementary upper contact surface is associated with a groove and is inclined downwardly toward the bottom of the groove.

10 Claims, 18 Drawing Sheets

(51) Int. Cl.
*E04C 2/38* (2006.01)
*E04F 13/08* (2006.01)

(56) References Cited

U.S. PATENT DOCUMENTS

| | | | | |
|---|---|---|---|---|
| 3,204,380 | A * | 9/1965 | Wilson | E04B 1/8409 |
| | | | | 52/144 |
| 7,506,481 | B2 * | 3/2009 | Grafenauer | E04L 35/12 |
| | | | | 52/592.1 |
| 8,205,404 | B2 * | 6/2012 | Vermeulen | B44C 5/04 |
| | | | | 52/311.2 |
| 8,591,691 | B2 * | 11/2013 | Wallin | E04F 15/02033 |
| | | | | 156/257 |
| 2005/0050827 | A1 | 3/2005 | Schitter | |
| 2005/0241255 | A1 * | 11/2005 | Kim | E04F 15/02 |
| | | | | 52/591.4 |
| 2008/0005999 | A1 * | 1/2008 | Pervan | B27F 5/026 |
| | | | | 52/589.1 |
| 2008/0168737 | A1 * | 7/2008 | Pervan | E04F 15/02 |
| | | | | 52/589.1 |
| 2008/0263987 | A1 * | 10/2008 | Leopolder | E04F 13/08 |
| | | | | 52/588.1 |
| 2009/0260313 | A1 * | 10/2009 | Segaert | E04F 15/02 |
| | | | | 52/592.1 |
| 2010/0018149 | A1 | 1/2010 | Thiers | |
| 2011/0138722 | A1 | 6/2011 | Hannig | |
| 2011/0167744 | A1 | 7/2011 | Whispell | |
| 2012/0304581 | A1 * | 12/2012 | Kim | E04F 15/105 |
| | | | | 52/588.1 |
| 2015/0107178 | A1 * | 4/2015 | Meersseman | B27N 7/00 |
| | | | | 52/313 |

FOREIGN PATENT DOCUMENTS

| | | |
|---|---|---|
| DE | 202014010455 A1 | 8/2015 |
| EP | 0220389 A2 | 5/1987 |
| EP | 1683929 A2 * | 7/2006 |
| FR | 2808824 A1 | 11/2016 |
| WO | WO 2009077178 A1 * | 6/2009 |

* cited by examiner

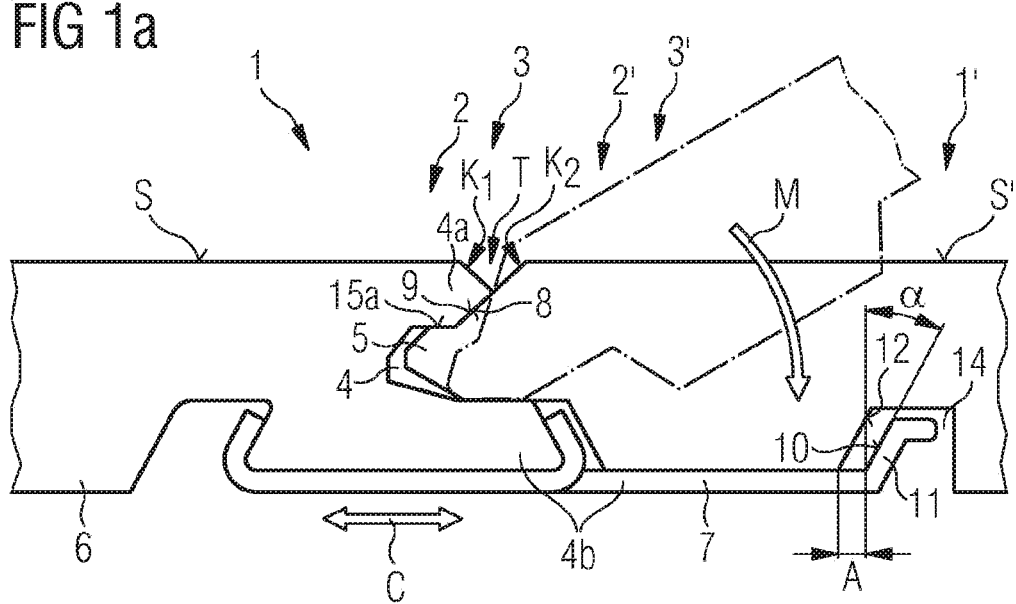
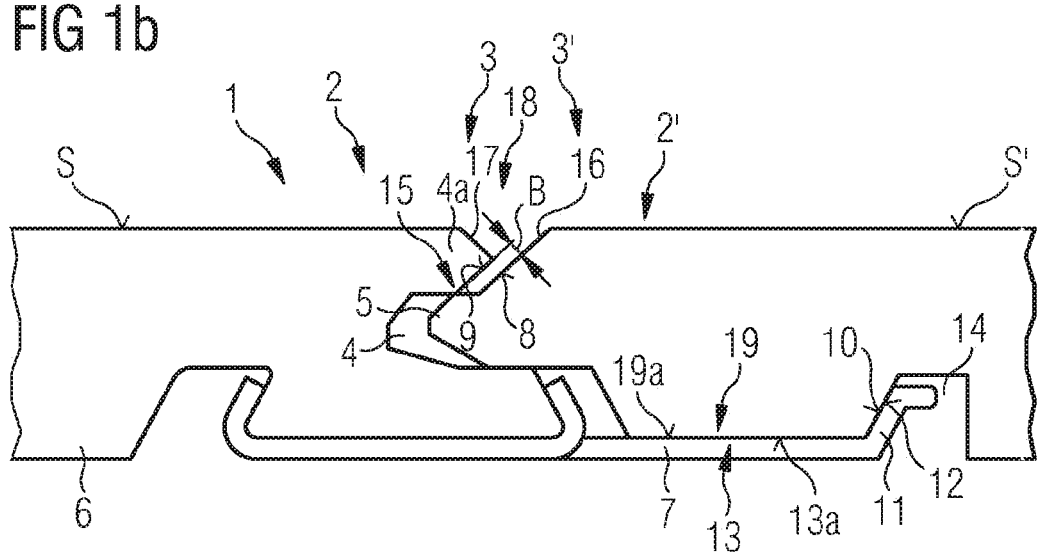

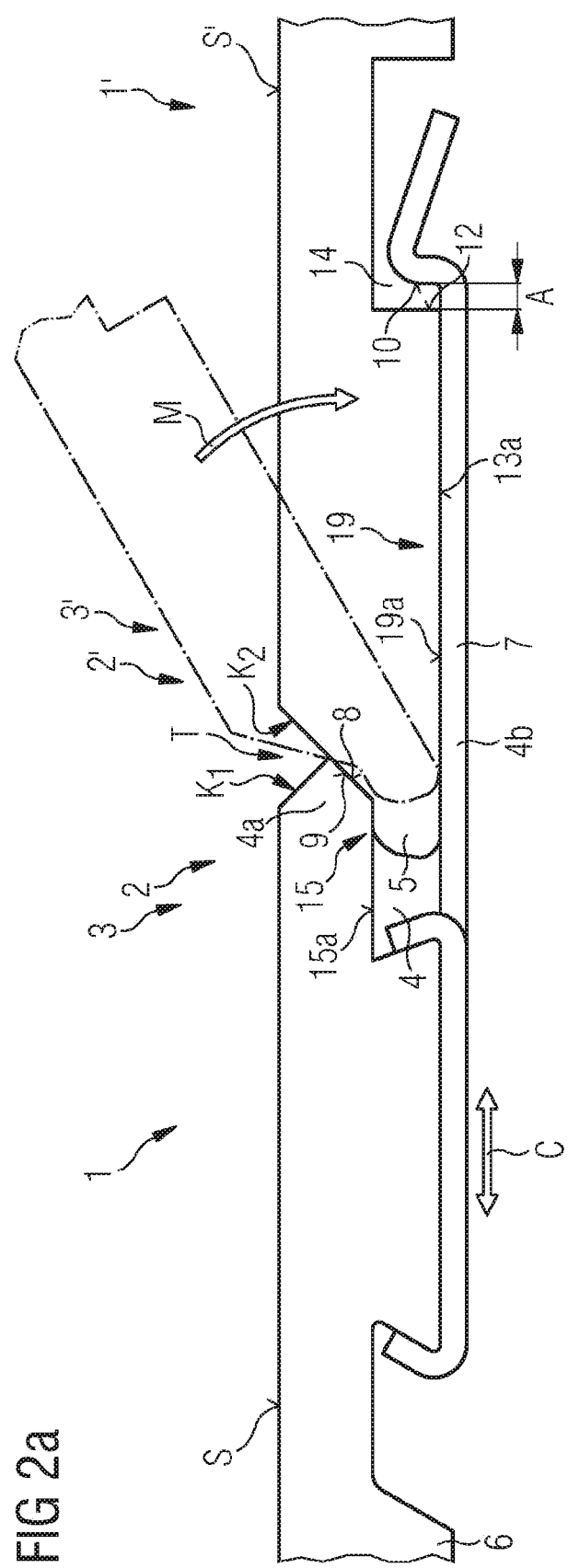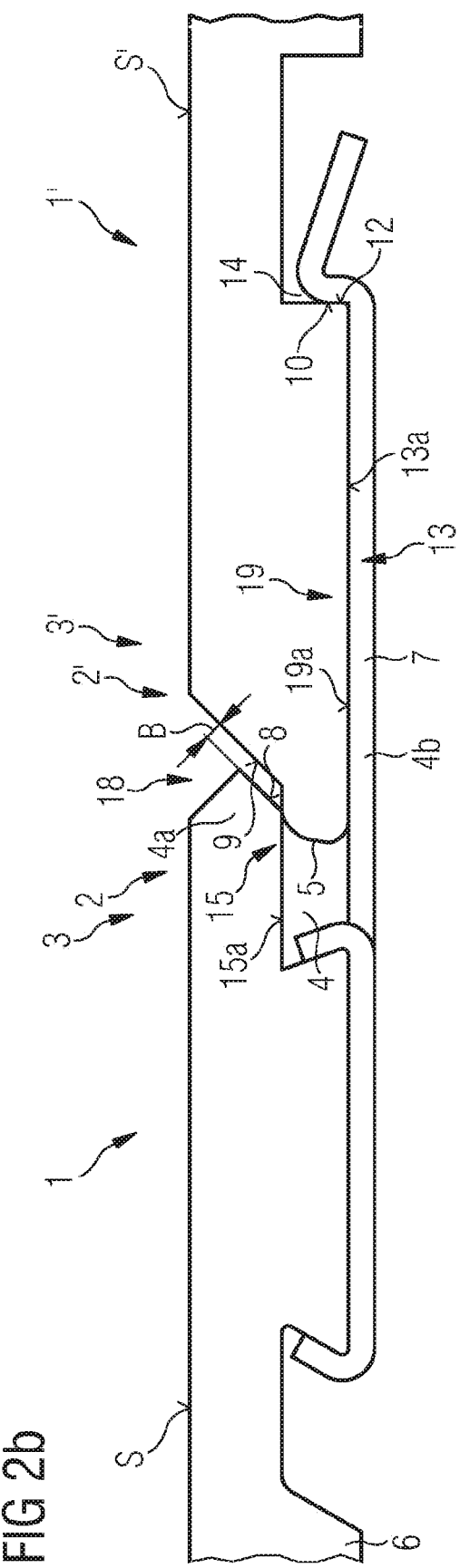

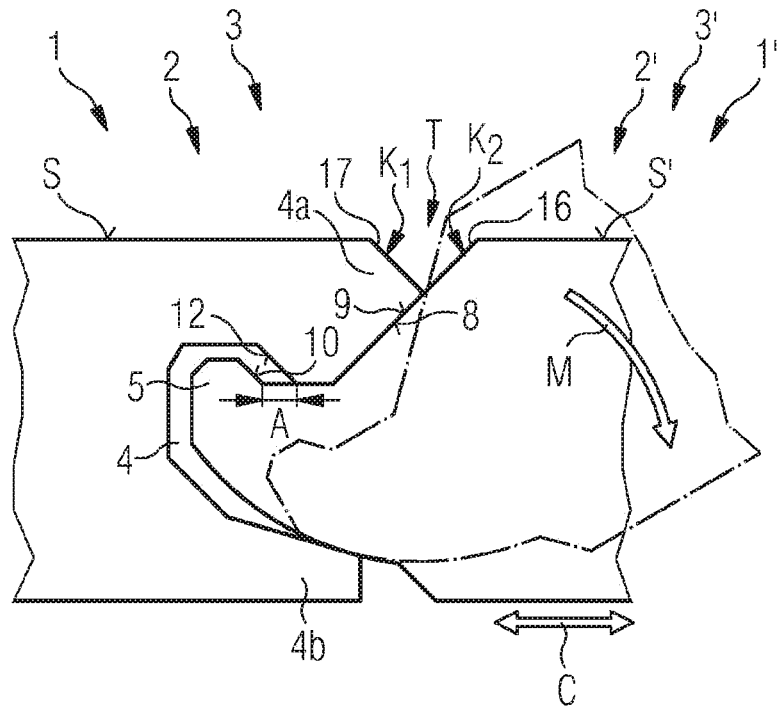
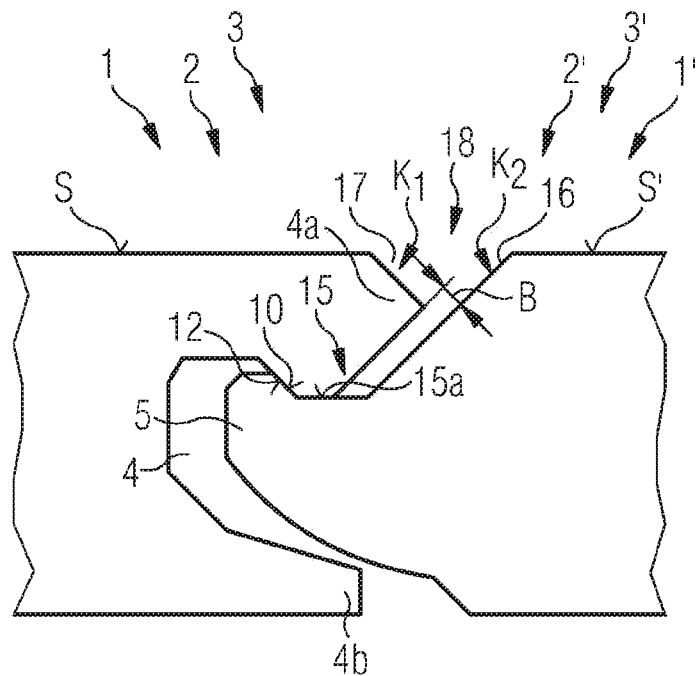

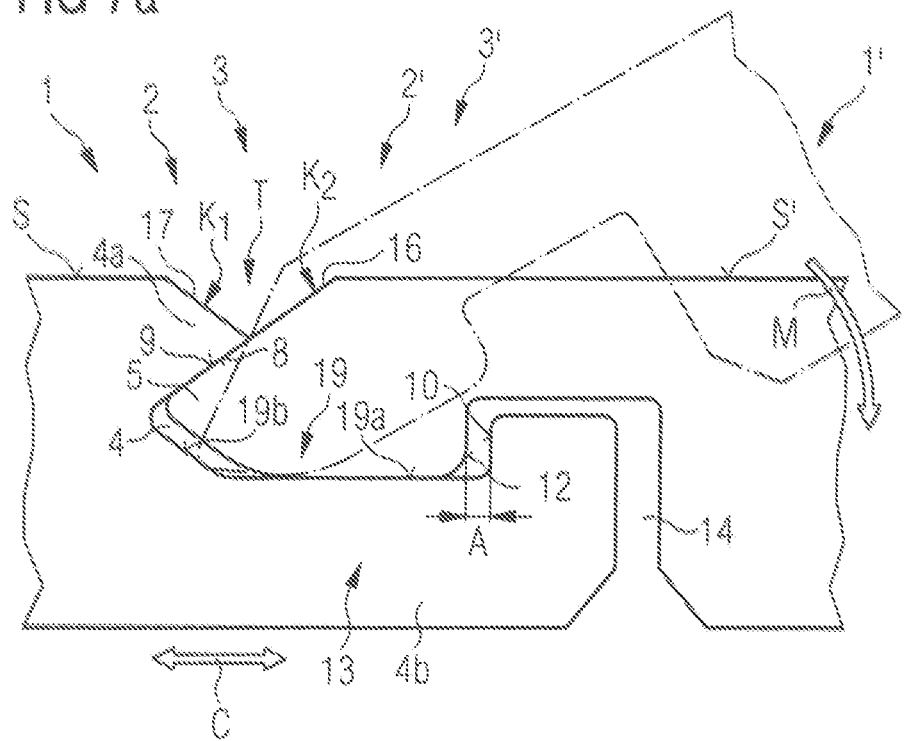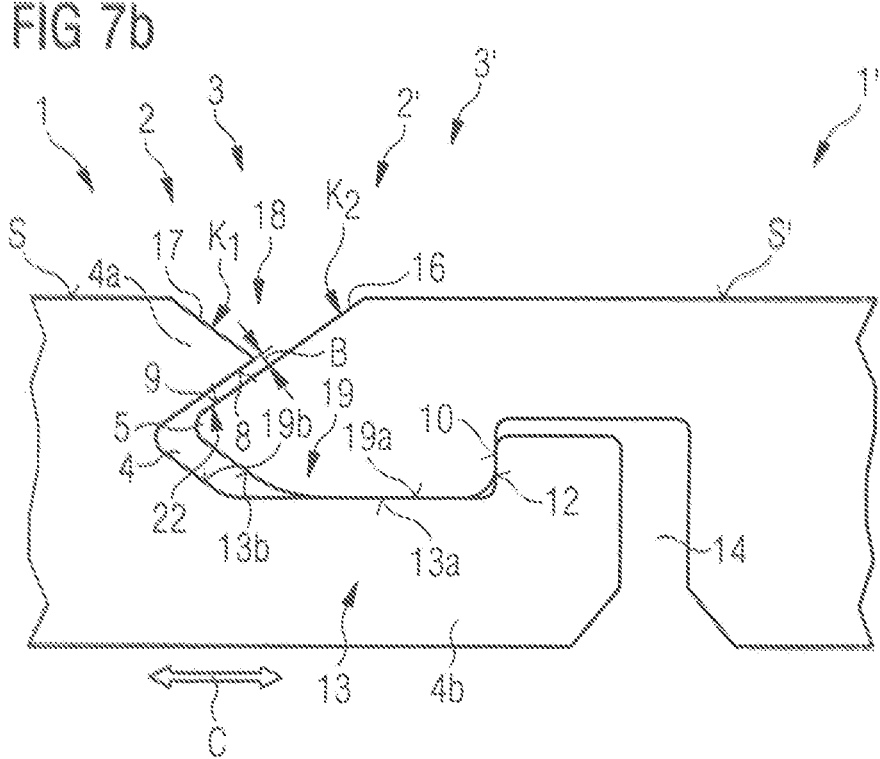

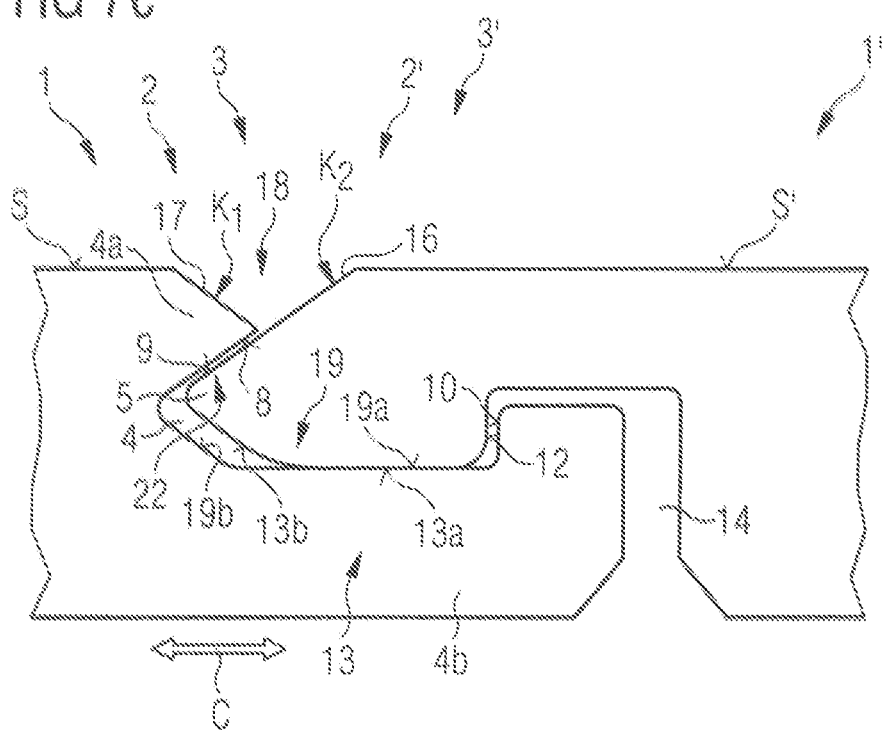

PANEL WITH COMPLIMENTARY LOCKING ELEMENTS

The present application is a 371 of International application PCT/EP2015/072564, filed Sep. 30, 2015, which claims priority of DE 10 2014 114 250.0, filed Sep. 30, 2014, the priority of these applications is hereby claimed and these applications are incorporated herein by reference.

BACKGROUND OF THE INVENTION

The invention concerns a panel comprising at least one pair of complementary locking means at mutually opposite panel edges, wherein the locking means are in the form of positively locking holding profiles with a locking groove and with a complementary locking tongue respectively, wherein at least at the edge of one of the holding profiles the panel surface has an edge break portion, with the proviso that that holding profile which is provided with the edge break portion is provided with an upper contact surfaced beneath the edge break portion and the complementary holding profile is provided with a complementary upper contact surface which is arranged substantially parallel thereto, and wherein a butt joint can be produced by the two contact surfaces in contact with each other, wherein the butt joint is inclined relative to the panel surface and for that purpose one of the contact surfaces is associated with a tongue and is inclined downwardly in the direction of the free end of the tongue in question and the complementary upper contact surface is associated with a groove and is inclined downwardly in the direction of the bottom of the groove in question.

Panels of that kind are used for example to produce floor coverings, in particular being suitable for floatingly laid floor coverings. The panels usually have decorative surfaces.

DE 20 2008 011 589 discloses a panel which has upper contact surfaces, between which a gap can be formed. An edge break portion is proposed, which provides that a gap which occurs is less conspicuous than in the case of a floor covering comprising panels without an edge break portion, which afford a flat floor surface so that gaps show themselves as being clearly visible. The edge break portion of the panels forms for example a V-shaped joint. A gap does not then appear at the surface of the panel, but at the deepest point of such a V-shaped joint, and is then not at all visible for a viewing person in accordance with a respective viewing direction from above. As a result the appearance of a floor covering is less unsightly by virtue of the V-shaped joint or the edge break portion, than in the case of a floor covering comprising panels which does not have an edge break portion and gaps are clearly visible at the surface of a floor covering.

A generic panel is known from US 2010/0018149 A1, namely the embodiment of FIG. 12. Therein a panel is proposed which has complementary locking means is provided on opposing panel edges, wherein one panel edge has an edge break portion and the complementary panel edge also has an edge break portion, which together with the aforementioned edge break portion form a V-groove. The butt joint under the V-groove is inclined relative to the panel surface and has a gap. A small wedge-shaped spring is associated with one of the contact surfaces, which spring is arranged on the upper edge of the panel and is inclined downward in the direction of its free end. A small wedge-shaped groove is associated with the complementary upper contact surface, which groove is located at the upper edge of the complementary panel. This upper contact surface is inclined downwards towards the bottom of the respective groove. The wedge-shaped spring and the wedge-shaped groove contribute, according to this prior art, if at all, only insignificantly to the vertical locking; instead, a tongue and groove is provided elsewhere specifically for the purpose of vertical locking, noted with V1. In this prior art, a locking is to be provided which can produce a relative position of the panels, which is referred to as initially interlocking position. From this position the panels are then movable in the horizontal direction toward or away from each other. In both directions a restoring force should be generated, namely for resetting towards the initially interlocking position. The restoring action is based on an elastic bending of the lower groove wall. Moreover, the lock in the horizontal direction is to be free of play, in which a horizontal position in which the lower groove wall is elastically bent downward is referred to within the meaning of this prior art as free of play.

It is therefore a disadvantage of the above prior art that the panel surface of that panel with the spring provided for the purpose of vertical locking may drop below the level that its panel surface had, as the initially mutually locking position has been taken. The design favors a vertical offset between the locked panel edges, wear of the locking means is amplified and the cohesion of locked panel edges is weakened.

SUMMARY OF THE INVENTION

The present-invention has the objective to provide a panel whose locking means hold together better when locked panel edges are moved away from one another.

According to the invention that object is attained in that the complementary holding profiles are desirably of such a configuration that they can be connected in positively locking relationship by a pivotal movement, with the proviso that a closed butt joint can be produced at the panel surface of two connected panel edges, with the proviso that a first range end of a scope for movement is defined by the two contact surfaces in contact with each other, more specifically for a movement of the panels relative to each other and in a direction of movement which is both perpendicular to the positively lockingly connected panel edges and also parallel to the plane of the connected panels, wherein each of the holding profiles has a respective lower abutment surface which are then spaced at their maximum from each other when the upper contact surfaces are in contact with each other and the butt joint is closed, and wherein the maximum spacing between the lower abutment surfaces determines the size of the scope for movement, and wherein the lower abutment surfaces, when they are in contact with each other, define the second range end of the scope for movement.

In a simple embodiment the tongue in question, at which the upper abutment surface is provided, is formed by the locking tongue and the groove in question, that is provided with the upper abutment surface, is formed by the locking groove. In addition then the lower abutment surface of the one holding profile is provided at the underside of the locking tongue and the abutment surface of the complementary holding profile is provided at the lower groove wall of the locking groove.

When two panels are locked together the mutually oppositely disposed contact surfaces extend with an inclination relative to the perpendicular to the panel surface. The upper contact surfaces are preferably arranged parallel to each other. The parallel arrangement means that the contact surfaces can then be in flat surface contact with each other when the butt joint is closed. The contact surfaces then fit snugly against each other. If two locked panels are moved away from each other and a gap is formed between the contact surfaces, then the width of that gap (gap dimension) is always less than the associated horizontal displacement travel by which the panels moved apart. In trigonometric terms the displacement of the panels can be viewed as the hypotenuse of a right-angled triangle while the gap dimension then corresponds to one of the sides of that triangle. Advantageously, a narrowed gap disrupts the appearance of a floor covering to a lesser degree than in the state of the art. A further advantage is that one of the two contact surfaces is always concealed to a viewer and is not visible at all. Because of its inclination relative to the perpendicular to the panel surface the other contact surface desirably does not allow a deep view into the gap. The smaller the inclination, the correspondingly less is the possible depth of view into the gap.

In addition a narrowed gap affords a further advantage, namely because dirt can less easily penetrate than into a gap which is of a greater width.

The present invention is intended for panels with a carrier plate or body of wood or of wood materials which have been subjected to further processing, but also for panels with a body of plastic or a wood-plastic composite material (referred to as wood particle composite (WPC)). In composite materials wood can also be replaced by organic and/or mineral fillers or can be supplemented by such materials, for example stone dust, ash, carbon black, crushed vegetable constituents like rice bran, bamboo or cork constituents and so forth. The structure of the carrier plates of composite material or those comprising wood particle composite can include a plurality of layers which involve differing compositions and differing properties, for example an elastic layer having damping properties or a diffusion or barrier layer which influence moisture permeability and so forth.

If a carrier plate is produced for a composite material or from a wood particle composite and a panel has been produced from that carrier plate, then growth can occur at the beginning of the life cycle of the panel, caused by a certain absorption of moisture. The maximum absorption capability for moisture is however limited and differs depending on the respective composition of the carrier plate. As soon as the panel has reached a certain degree of moisture saturation a growth state occurs, which then varies only within relatively small limits and more specifically then substantially because of climatic changes. Both changes in the ambient temperature and also air humidity in the immediate environment influence the size of the panel and can cause a certain degree of shrinkage or a certain degree of expansion.

When a floor covering is composed of such panels that gives a floor pad. A certain degree of shrinkage or expansion of the individual panels builds up and leads to shrinkage or expansion of the floor pad overall. Desirably the scope for movement within locked panel edges is of such a size that ideally all panels can shrink by the maximum extent, without transmitting substantial tensile forces to the adjacent panels, and likewise ideally all panels can expand by the maximum amount, without transmitting substantial compressive forces to the adjacent panels. Therefore sufficient space is provided for each panel to be able to expand or shrink to the extent as is required on the one hand in order to prevent the floor covering from heaving up or on the other hand in order to avoid gapping which exceeds the maximum size of a gap B and would damage the panel edges.

If the body at least partially comprises a plastic then a design configuration can comprise a body of a plastic or a wood particle composite (WPC). The carrier plate or the body is for example formed from a thermoplastic, elastomeric or thermosetting plastic. It is also possible to use recycling materials from the specified materials in accordance with the invention. Preferably in that respect plate materials are used, in particular of thermoplastic plastic material like polyvinylchloride, polyolefins (for example polyethylene (PE), polypropylene (PP), polyamides (PA), polyurethane (PU), polystyrene (PS), acrylonitrile-butadiene-styrene (ABS), polymethylmethacrylate (PMMA), polycarbonate (PC), polyethyleneterephthalate (PET), polyetheretherketone (PEEK) or mixtures or co-polymers. In that respect, irrespective of the base material of the carrier plate, it is possible to provide for example plasticizers which can be present for example in a range of between $\geq 0$ wt. % and $\leq 20$ wt. %, in particular $\leq 10$ wt. %, preferably $\leq 7$ wt. %, for example in a range of between $\geq 5$ wt. % and $\leq 10$ wt. %. A suitable plasticizer includes for example the plasticizer marketed by BASF under the trade name "Dinsch". In addition copolymers like for example acrylates or methacrylates can be provided as a substitute for conventional plasticizers.

In particular thermoplastic plastics also afford the advantage that the products made therefrom can be very easily recycled. It is also possible to use recycling materials from other sources. That affords a further option for reducing manufacturing costs.

In that case such carrier plates are very elastic or resilient, which allows a comfortable impression when walking thereon, and in addition the noise occurring when walking thereon can be reduced in comparison with conventional materials so that it is possible to achieve improved footfall sound damping.

In addition the above-mentioned carrier plates afford the advantage of good water resistance as they involve swelling of 1% or less. Besides pure plastic carriers that surprisingly also applies to WPC materials, as are discussed in detail hereinafter.

In particularly advantageous fashion the carrier material can have or can comprise wood plastic composite (WPC). Here for example a wood and a polymer may be suitable, which can be present in a ratio of between 40/60 and 70/30, for example 50/50. For example polypropylene, polyethylene or a copolymer of the two above-mentioned materials can be used as polymer constituents. Such materials afford the advantage that they can already be shaped into a carrier plate at low temperatures like for example in a range of between $\geq 180°$ C. and $\leq 200°$ C. in the above-described method so that it is possible to enable particularly effective process implementation, for example with line speeds by way of example in a region of 6 m/min. For example they are possible for a WPC product with a 50/50 distribution of the wood and polymer components, with a product thickness by way of example of 4.1 mm, which can permit a particularly effective manufacturing process.

In addition it is thus possible to produce highly stable panels which further have a high degree of elasticity, which can further be advantageous in regard to footfall sound damping, in particular for an effective and inexpensive design configuration of connecting elements at the edge region of the carrier plate. In addition the above-mentioned good water compatibility can also be achieved with a swelling of less than 1%, with such WPC materials. In that respect WPC materials may have for example stabilizers and/or other additives which can preferably be present in the plastic component.

In addition it can be particularly advantageous for the carrier plate to include or comprise a PVC-based material. Such materials can also serve in particularly advantageous manner for high-quality panels which for example can also be used without problem in wet rooms. In addition PVC-based materials for the carrier plate are also suitable for a particularly effective manufacturing process as here about line speeds of 8 m/min can be possible with a product thickness by way of example of 4.1 mm, which can permit a particularly effective manufacturing process. In addition such carrier plates also have advantageous elasticity and water compatibility, which can lead to the above-mentioned advantages.

In the case of plastic-based panels, like also in the case of WPC-based panels, mineral fillers can be advantageous. Particularly appropriate here are for example talcum or also calcium carbonate (chalk), aluminum oxide, silica gel, quartz powder, wood dust, and gypsum. By way of example chalk can be provided in a range of between ≥30 wt. % and ≤70 wt. %, wherein in particular slipping of the carrier plate can be improved by the fillers, in particular the chalk. They can also be colored in known fashion. In particular it can be provided that the material of the carrier plates has a flame resistance agent.

In a particularly preferred configuration of the invention the material of the carrier plate comprises a mixture of a PE/PP block copolymer with wood. In that respect the proportion of PE/PP block copolymer and the proportion of the wood can be between ≥45 wt. % and ≤55 wt. %. In addition the material of the carrier plate can have between ≥0 wt. % and ≤10 wt. % of further additives like for example flow adjuvants, thermostabilizers or UV-stabilizers. In that respect the particle size of the wood is between >0 μm and ≤600 μm with a particularly preferred D50 particle size distribution of ≥400 μm. In particular the material of the carrier plate can have wood with a D10 particle size distribution of ≥400 μm. In that case the particle size distribution is related to the volumetric diameter and refers to the volume of the particles. Particularly preferably the material of the carrier plate is prepared in the form of a granulated or pelletized pre-extruded mixture of a PE/PP block copolymer with wood particles of the specified particle size distribution. The granules and/or the pellets can preferably be for example of a grain size in a range of between ≥400 μm and ≤10 mm, preferably ≥600 μm and ≤10 mm, in particular ≥800 μm and ≤10 mm.

In a further preferred configuration of the invention the carrier plate comprises a mixture of a PE/PP polymer blend with wood. In that case the proportion of the PE/PP polymer blend and the proportion of the wood can be between ≥45 wt. % and ≤55 wt. %. In addition the material of the carrier plate can have between ≥0 wt. % and ≤10 wt. % of further additives like for example flow adjuvants, thermostabilizers or UV-stabilizers. The particle size of the wood is between >0 μm and ≤600 μm with a particularly preferred D50 particle size distribution of ≥400 μm. In particular the material of the carrier plate can have wood with a D10 particle size distribution of ≥400 μm. In that case the particle size distribution is related to the volumetric diameter and refers to the volume of the particles. Particularly preferably the material of the carrier plate is prepared in the form of a granulated or pelletized pre-extruded mixture of a PE/PP polymer blend with wood particles of the specified particle size distribution. The granules and/or the pellets can preferably be for example of a grain size in a range of between ≥400 μm and ≤10 mm, preferably ≥600 μm and ≤10 mm, in particular ≥800 μm and ≤10 mm.

In a further configuration of the invention the material of the carrier plate comprises a mixture of a PP homopolymer with wood. In that case the proportion of the PP homopolymer and the wood proportion can be between ≥45 wt. % and ≤55 wt. %. In addition the material of the carrier plate can have between ≥0 wt. % and ≤10 wt. % of further additives like for example flow adjuvants, thermostabilizers or UV-stabilizers. The particle size of the wood is between ≥0 μm and ≤600 μm with a particularly preferred D50 particle size distribution of ≥400 μm. In particular the material of the carrier plate can have wood with a D10 particle size distribution of ≥400 μm. In that case the particle size distribution is related to the volumetric diameter and refers to the volume of the particles. Particularly preferably the material of the carrier plate is prepared in the form of a granulated or pelletized pre-extruded mixture of a PP homopolymer with wood particles of the specified particle size distribution. The granules and/or the pellets can preferably be for example of a grain size in a range of between ≥400 μm and ≤10 mm, preferably ≥600 μm and ≤10 mm, in particular ≥800 μm and ≤10 mm. In a further configuration of the invention the material of the carrier plate comprises a mixture of a PVC polymer with chalk. In that case the proportion of the PVC polymer and the chalk proportion can be between ≥45 wt. % and ≤55 wt. %. In addition the material of the carrier plate can have between ≥0 wt. % and ≤10 wt. % of further additives like for example flow adjuvants, thermostabilizers or UV-stabilizers. The particle size of the chalk is between >0 μm and ≤600 μm with a preferred D50 particle size distribution of ≥400 μm. In particular the material of the carrier plate can have chalk with a D10 particle size distribution of ≥400 μm. In that case the particle size distribution is related to the volumetric diameter and refers to the volume of the particles. Particularly preferably the material of the carrier plate is prepared in the form of a granulated or pelletized pre-extruded mixture of a PVC polymer with chalk of the specified particle size distribution. The granules and/or the pellets can preferably be for example of a grain size in a range of between ≥400 μm and ≤10 mm, preferably ≥600 μm and ≤10 mm, in particular ≥800 μm and ≤10 mm.

In a further configuration of the invention the material of the carrier plate comprises a mixture of a PVC polymer with wood. In that case the proportion of the PVC polymer and the wood proportion can be between ≥45 wt. % and ≤55 wt. %. In addition the material of the carrier plate can have between ≥0 wt. % and ≤10 wt. % of further additives like for example flow adjuvants, thermostabilizers or UV-stabilizers. The particle size of the wood is between >0 μm and ≤600 μm with a preferred D50 particle size distribution of ≥400 μm. In particular the material of the carrier plate can have wood with a D10 particle size distribution of ≥400 μm. In that case the particle size distribution is related to the volumetric diameter and refers to the volume of the particles. Particularly preferably the material of the carrier plate is prepared in the form of a granulated or pelletized pre-extruded mixture of a PVC polymer with wood particles of the specified particle size distribution. The granules and/or the pellets can preferably be for example of a grain size in a range of between ≥400 μm and ≤10 mm, preferably ≥600 μm and ≤10 mm, in particular ≥800 μm and ≤10 mm.

To determine the particle size distribution it is possible to have recourse to the generally known methods like for example laser diffractometry, with that method it is possible to determine particle sizes in the range of some nanometers up to several millimeters. It is thus also possible to ascertain D50 and D10 values respectively, with which 50% and 10% respectively of the measured particles are smaller than the specified value.

In accordance with a further configuration of the invention the carrier material has a matrix material having a plastic and a solids material, wherein the solids material is formed by talcum in respect of at least 50 wt. %, in particular at least 80 wt. %, particularly preferably at least 95 wt. %, with respect to the solids material. In that respect the matrix material is provided in an amount, with respect to the carrier material, of between ≥30 wt. % and ≤70 wt. %, in particular ≥40 wt. % and ≤60 wt. %, and the solids material, in relation to the carrier material, is present in an amount with respect to the carrier material of between ≥30 wt. % and ≤70 wt. %, in particular ≥40 wt. % and ≤60 wt. %, for example less than or equal to 50 wt. %. It is further provided that the carrier material and the solids material jointly, in relation to the carrier material, are present in an amount of ≥95 wt. %, in particular ≥99 wt. %.

In such a configuration of the invention the solids material can be formed by talcum in respect of at least 50 wt. %, in particular at least 80 wt. %, for example 100%, with respect to the solids material. In that respect the term talcum is used in per se known manner to denote a magnesium silicate hydrate which for example can be of the chemical formula $Mg_3[Si_4O_{10}(OH)_2]$. Thus the solids component is advantageously formed at least by a large part from the mineral substance talcum, wherein that substance can be used for example in powder form or can be present in the carrier material in the form of particles. In principle the solids material can comprise a powder solid.

It may be advantageous if the specific BET surface density, in accordance with ISO 4652, of the talcum particles is in a range of between ≥4 m2/g and ≤8 m2/g, for example in a range of between ≥5 m2/g and ≤7 m2/g.

It may further be advantageous if the talcum is present with a bulk density in accordance with DIN 53468, in a range of between ≥0.15 g/cm3 and ≤0.45 g/cm3, for example in a range of between ≥0.25 g/cm3 and ≤0.35 g/cm3.

The matrix material in such a configuration of the invention serves in particular to receive or embed the solids material, in the carrier in the finished condition. In that respect the matrix material has a plastic or a plastic mixture. In particular in regard to the method of manufacture, as is described in detail hereinafter, it may be advantageous if the matrix material has a thermoplastic plastic. That makes it possible for the carrier material or a component part of the carrier material to have a melting point or a softening point in order to shape the carrier material by the action of heat in a further method step, as is described in detail hereinafter with reference to the method. The matrix material can comprise in particular a plastic or a plastic mixture and optionally a bonding agent. Preferably those components can constitute at least 90 wt. %, particularly preferably at least 95 wt. %, in particular at least 99 wt. %, of the matrix material.

It can further be provided that the matrix material is present in an amount, with respect to the carrier material, of ≥30 wt. % and ≤70 wt. %, in particular ≥40 wt. % and ≤60 wt. %. It is further provided that the solids material, with respect to the carrier material, is present in an amount with respect to the carrier material of between ≥30 wt. % and ≤70 wt. %, in particular between ≥40 wt. % and ≤60 wt. %.

Polypropylene is particularly suitable as the matrix material as on the one hand it can be inexpensively obtained and in addition as a thermoplastic plastic has good properties as a matrix material for embedding the solids material. In that respect in particular a mixture of a homopolymer and a copolymer for the matrix material permit particularly advantageous properties to be achieved. Such materials further have the advantage that they can already be shaped in the above-described method to form a carrier, at low temperatures like for example in a range of between ≥180° C. and ≤200° C. so that they permit particularly effective process implementation, for example at line speeds by way of example in a region of 6 m/min.

It may further be advantageous if the homopolymer has a tensile strength in accordance with ISO 527-2 which is in a range of between ≥30 MPa and ≤45 MPa, for example in a range of between ≥35 MPa and ≤40 MPa, to achieve good stability.

Furthermore, in particular for good stability, it can be advantageous if the homopolymer has a bending modulus in accordance with ISO 178 in a range of between ≥1000 MPa and ≤2200 MPa, for example in a range of between ≥1300 MPa and ≤1900 MPa, for example in a range of between ≥1500 MPa and ≤1700 MPa.

In regard to tensile deformation of the homopolymer in accordance with ISO 527-2 it may further be advantageous if that is in a range of between ≥5% and ≤13%, for example in a range of between ≥8% MPa and ≤10%.

For particularly advantageous manufacturing implementation it may be provided that the Vicat softening temperature in accordance with ISO 306/A for an injection-molded component is in a range of between ≥130° C. MPa and ≤170° C., for example in a range of between ≥145° C. and ≤158° C.

It may further be advantageous if the solids material, besides talcum, has at least one further solid. That configuration can make it possible in particular for the weight of the carrier material or a panel formed with the carrier material, compared to a carrier material or panel, in which the solids material comprises talcum, to be markedly reduced. Thus the solid added to the solids material can be in particular of a reduced density in comparison with talcum. For example the added solid can be of a bulk density in a range of ≤2000 kg/m3, in particular ≤1500 kg/m3, for example ≤1000 kg/m3, particularly preferably ≤500 kg/m3. In that respect, in dependence on the solid added, a further adaptability to the desired, in particular mechanical properties, can be rendered possible.

For example the further solid can be selected from the group consisting of wood, for example in the form of wood dust, expanded clay, volcanic ash, pumice, aerated concrete, in particular inorganic foams, and cellulose. In regard to aerated concrete that can be for example the solid used by Xella under the brand name YTONG, which substantially comprises quartz sand, lime and cement, or the aerated concrete can have the above-mentioned constituents. In regard to the added solid that can be made up for example from particles of the same particle size or particle size distribution, as the particle sizes or particle size distributions described hereinbefore for talcum. The further solids can be present in particular in a proportion in the solids material, that is in a range of <50 wt. %, in particular <20 wt. %, for example <10 wt. %, further by way of example <5 wt. %.

Alternatively for wood, in particular for wood dust, it can be provided that the particle size thereof is between >0 μm and ≤600 μm, with a preferred D50 particle size distribution of ≥400 μm.

In a further configuration the material of the carrier plate can have hollow microspheres. Such additives can provide in particular that the density of the carrier plate and thus the panel produced can be significantly reduced so that it is possible to ensure particularly simple and inexpensive transport and in addition particularly convenient laying. In that respect in particular the inclusion of hollow microspheres can ensure a stability of the panel produced, which is not significantly reduced in comparison with a material without hollow microspheres. Thus for a large part of the applications the stability is completely sufficient. In that respect the term hollow microspheres can be interpreted as meaning in particular structures which have a hollow main body and are of a size or a maximum diameter which is in the micrometer range. For example hollow spheres which can be used can be of a diameter which is in the range of between $\geq 5$ μm and $\leq 100$ μm, for example $\geq 20$ μm and $\leq 50$ μm. In principle any material like for example glass or ceramic falls to be considered as the material of the hollow microspheres. In addition, by virtue of the weight, plastics, for example the plastics also used in the carrier material, like for example PVC, PE or PP, may be advantageous, in which respect they can possibly be prevented from deformation during the manufacturing method, for example by means of suitable additives.

The hardness of the material of the carrier plate can involve values in a range of 30-90 N/mm$^2$ (measured in accordance with Brinell). The modulus of elasticity can be in a range of between 3000 and 7000 N/mm$^2$.

The invention is preferably provided for panels of an overall thickness of 2 mm and more. For panels whose overall thickness is less than 4 mm preferably carrier plates with a predominant plastic component are used.

A development provides that at the edge of the holding profile which has the locking tongue there is provided an edge break portion, that the edge break portion is in the form of a chamfer, that the chamfer is inclined downwardly towards the free end of the locking tongue and that the upper contact surface of said holding profile is also inclined downwardly towards the free end of the locking tongue, wherein the angle of inclination of the upper contact surface is less than or equal to or larger than the angle of inclination of the chamfer.

In this embodiment at the panel edge provided with the locking tongue, the chamfer and the upper contact surface are inclined downwardly in the same direction. Other embodiments however involve a departure from that principle, more specifically those which, on a holding profile, in addition to the locking tongue, also have a closure groove because then the upper contact surface is associated with the closure groove and for that reason must involve an opposite inclination, as is set forth hereinafter.

The panel is of a particularly simple configuration if the tongue top side of the locking tongue is inclined in relation to the panel surface and the tongue top side and the upper contact surface are integrated to constitute a common surface, wherein the locking groove at the inside of its upper groove wall is also inclined in relation to the panel surface and wherein the inclination thereof is matched to the inclination of the upper contact surface of the locking tongue.

The tongue top side and the contact surface are integrated to constitute a surface. That results in dispensing with a notch location or a bend point between the tongue top side and the contact surface. Because this saves on a notch location in the contour the holding profile enjoys greater strength. In addition the contour overall is of a simpler configuration and for that reason is better suited for very thin panels. The smaller the overall thickness of the panel is, then the correspondingly simpler should the configuration of the holding profile be because in particular a contour involving very fine details is more difficult to produce, the thinner the panel is.

A further benefit is afforded if the locking groove has a lower groove wall, at the free end of which there is provided a holding edge directed towards the panel top side, that the lower abutment surface of the locking groove is arranged at the holding edge of the lower groove wall and that the perpendicular on the lower abutment surface is directed inwardly towards the bottom of the locking groove. It has been found that locking with lower abutment surfaces is particularly durable and stable if such locking is implemented spaced from the panel surface in the region of a lower groove wall.

The inventor looked for the reason why elastic bending of the lower groove wall of the locking groove forces the contact surfaces of locked panels towards each other, and found in that respect that, of the lower abutment surfaces, at least the abutment surface of the locking groove can be arranged perpendicularly in relation to the panel surface in order to avoid the panels being forced towards each other.

Desirably a tongue underside of the locking tongue has a lower contacting surface and a lower groove wall of the locking groove is provided with a support surface for the lower contacting surface of the locking tongue, wherein the lower contacting surface of the locking tongue is arranged parallel to the panel surface and the support surface also extends parallel to the panel surface.

That measure provides that the support surface for the lower contacting surface is arranged horizontally in the position of use. The flat contact surface of the locking tongue can then divert forces acting from above to the also flat support surface of the lower groove wall. In addition the contacting surface and the support surface serve as mounting means and guide means when the panels, in the context of the existing freedom of movement, shift in their relative position with respect to each other.

A development of the panel provides that the tongue underside of the locking tongue, at least at one of the two ends, has a lower contacting surface and a rising region.

The joining operation is simplified by that configuration. The panel with the locking tongue which is usually fitted in angled relationship (inclinedly) to the locking groove of a lying panel and is then inserted into the locking groove in positively locking relationship by means of a downward pivotal movement of the locking tongue can be more easily pivoted into the locking groove of a lying panel when the locking tongue has at least one rising region.

An alternative provides that the holding profile with the locking tongue has a closure groove above the locking tongue and the complementary holding profile with the locking groove with its free end of the upper groove wall forms a closure tongue which can be inserted into the closure groove. As a result the locking tongue which is useful in terms of the strength of the locking connection and the locking groove are protected and remote from the location at which dirt can enter directly. The closure tongue/closure groove disposed in front of same keep dirt away from the locking tongue and the locking groove.

In the above-mentioned alternative the upper contact surface of that panel edge which is provided with the closure tongue is arranged at the tongue top side of the closure tongue and the upper contact surface of that panel edge which is provided with the closure groove is arranged at the upper groove wall of the closure groove.

The invention is shown by way of example hereinafter in a drawing and described in detail by means of a number of embodiments by way of example.

In the drawing:

BRIEF DESCRIPTION OF THE DRAWING

FIG. 1a shows a first embodiment of a panel according to the invention, wherein the panel is shown in separated relationship in order to illustrate the oppositely disposed panel edges thereof in the locked condition with the closed butt joint, FIG. 1b shows the embodiment of FIG. 1a with mutually contacting lower contact surfaces and a gap at the butt joint which is opened to its maximum, FIG. 2a shows a second embodiment of a panel according to the invention, wherein the panel is shown in separated relationship in order to illustrate the oppositely disposed panel edges thereof in the locked condition with the dosed butt joint, FIG. 2b shows the embodiment of FIG. 2a with mutually contacting lower contact surfaces and a gap at the butt joint which is opened to its maximum, FIG. 5a shows a fifth embodiment of a panel according to the invention, wherein the panel is shown in separated relationship in order to illustrate the oppositely disposed panel edges thereof in the locked condition with the closed butt joint, FIG. 5b shows the embodiment of FIG. 5a with mutually contacting lower contact surfaces and a gap at the butt joint which is opened to its maximum, FIG. 7a shows a seventh embodiment of a panel according to the invention, wherein the panel is shown in separated relationship in order to illustrate the oppositely disposed panel edges thereof in the locked condition with the closed butt joint, FIG. 7b shows the embodiment of FIG. 7a with mutually contacting lower contact surfaces and a gap at the butt joint which is opened to its maximum, FIG. 7c shows the embodiment of FIGS. 7a/7b with lower contact surfaces at a certain spacing from each other and with a certain gap at the opened butt joint.

DETAILED DESCRIPTION OF THE INVENTION

Figure 3A:
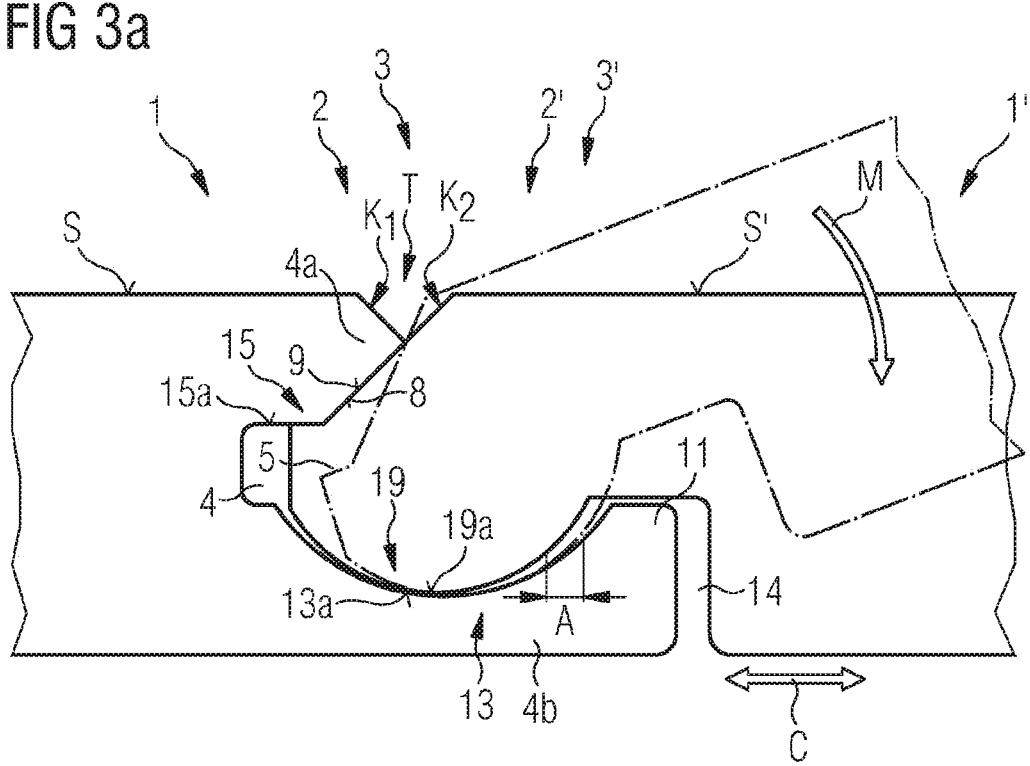
FIG. 3a shows a third embodiment of a panel according to the invention, wherein the panel is shown in separated relationship in order to illustrate the oppositely disposed panel edges thereof in the locked condition with the closed butt joint.

FIG. 1a shows a first embodiment of a panel according to the invention. The panel is shown in separated relationship in order to be able to show its oppositely disposed panel edges 1 and 1' in the locked condition with the closed butt joint. It will be appreciated that the panel edges of which portions are shown can also be viewed as a portion-wise view of two panels which are not separated.

In practice it is certainly usual if for example a panel at the end of a row of panels is too long, for that to be cut through to shorten it to the required length. In general a fresh row of panels can be begun with the cut-off residual portion. Complementary holding profiles of a cut panel fit into each other and in principle can be locked together, as shown in the present groups of FIGS. 1-15.

The panel 1 and 1' of Figures group 1 is based on a conventional structure from Valinge Innovation AB, as is known from WO 1994/026999. It has a pair of complementary locking means 2 and 2' at the illustrated mutually opposite panel edges. Those locking means are in the form of positively locking holding profiles 3 and 3' respectively with a locking groove 4 and with a complementary locking tongue 5 respectively. The locking groove 4 includes an upper groove wall 4a and a lower groove wall 4b. That holding profile with the locking groove 4 is made up in two pieces. One of the two component parts is a panel plate 6. Fixed at the edge thereof as a second component part in positively locking relationship is a separate strip 7 of another material. The separate strip 7 forms the lower groove wall 4b of the locking groove 4.

In comparison with the conventional panel it is modified in such a way that the panel surface S and S' respectively at the edges of both holding profiles 3 and 3' each have an edge break portion $K_1$ and $K_2$ respectively. Provided beneath the edge break portion is a respective upper contact surface, namely both at the holding profile 3 with the locking groove an upper contact surface 8, and also at the holding profile 3' with the locking tongue 5 an upper contact surface 9. In the position shown in FIG. 1a the panel edges 1/1' are butted together in such a way that the two upper contact surfaces 8 and 9 are in contact and a closed butt joint T is produced. The butt joint T is inclined relative to the panel surface S and S' respectively. One of the upper contact surfaces 9 is associated with the locking tongue 5 and that upper contact surface 9 is inclined downwardly in the direction of the free end of the locking tongue 5. The complementary upper contact surface 8 is associated with the locking groove 4 and that contact surface 8 is inclined downwardly in the direction of the bottom of the locking groove 4. The complementary holding profiles 3 and 3' are of such a configuration that they can be locked in positively locking relationship with each other by a pivotal movement M of the one panel 1' which is fitted with its locking tongue 5 inclinedly to the locking groove 4 of a lying panel 1. For that purpose a panel is usually applied in an inclined position, as shown by the panel edge in FIG. 1a, indicated in the form of a dash-dotted line, the same applying for the following Figure groups 2 through 15 in which an inclinedly fitted panel edge is also indicated by a dash-dotted line. That kind of locking action by means of a pivotal movement M makes it possible to produce the illustrated closed butt joint T between two panel edges 1 and 1'. The two contact surfaces 8 and 9 which are brought into contact with each other define a first range end of a scope for movement X, more specifically for a movement of the panel edges relative to each other and in a direction of movement which is both perpendicular to the positively lockingly connected panel edges and also parallel to the plane of the connected panels, as indicated by the double-headed arrow C.

In addition each of the holding profiles 3 and 3' has a respective lower abutment surface. A lower abutment surface 10 of the panel 1 which is provided with the locking groove 4 is disposed at the lower groove wall 4b of the locking groove 4. For that purpose the lower groove wall 4b is provided at its free end with a holding edge 11 directed towards the panel surface S'. The holding edge 11 has a free side which is directed towards the bottom of the locking groove 4 and at which the lower abutment surface 10 is formed.

In the embodiment in FIGS. 1a/1b that lower abutment surface 10 is arranged with an inclination through an angle α in relation to the perpendicular to the panel surface. A lower abutment surface 12 of the panel 1' which is provided with the locking tongue 5 is disposed at the tongue underside 13. This has an undercut 14 and thus forms a rearward side which is directed towards the core of the panel and at which the lower abutment surface 12 is formed. That lower abutment surface 12 of the locking tongue 5 is inclined through the same angle α in relation to the perpendicular to the panel surface S/S', as the lower abutment surface 10 of the locking groove 4.

The inclined position of the lower abutment surface 10 of the locking groove 4 forms an inclined plane and the lower groove wall 4b has a certain spring elasticity. When the lower groove wall 4b is bent elastically downwardly then a spring-elastic return force is produced in the lower groove wall 4b. If that return force presses against the lower abutment surface 12 of the locking tongue 5 then the panel edges 1 and 1' can be moved towards each other thereby so that a gap B present between the upper contact surfaces 8 and 9 is reduced in size. Preferably the travel movement of the panel edges towards each other, which can be produced solely by the return force, is not so great that the upper contact surfaces 8 and 9 could come into contact with each other.

If the upper contact surfaces 8 and 9 come into contact with each other and the butt joint T is closed then the lower abutment surfaces 10 and 12 are spaced from each other at their maximum. The horizontal spacing A shown in FIG. 1a between the lower abutment surfaces 10 and 12 determines the size of the scope of movement X for the panel edges 1 and 1' in the locked condition (A=X). If the spacing A between the lower abutment surfaces 10 and 12 is viewed as the hypotenuse of a right-angled triangle then the dimension of the gap B (gap width) corresponds to one of the sides of that triangle.

In FIG. 1b the two panel edges 1 and 1' are displaced relative to each other. The lower abutment surfaces 10 and 12 are in contact with each other and a gap A has been formed between the upper contact surfaces 8 and 9. In this position in which the lower abutment surfaces 10 and 12 are in contact with each other they define the second range end of the scope of movement X for the locked panel edges 1/1'.

Provided at a tongue top side 15 of the locking tongue 5 is a portion 15a extending parallel to the panel surface S' (horizontally). That portion 15a together with the locking groove 4 substantially provides for the strength of the locking connection in the vertical direction and also holds the panel surfaces S and S' in one plane and prevents unwanted heightwise displacement between the panels surfaces S and S'.

The upper contact surface 9 is arranged above that portion 15a and the edge break portion $K_2$ in the form of a chamfer 16 is disposed above the contact surface 9. The inclination of the chamfer 16 and the inclination of the upper contact surface 9 are the same. The edge break portion $K_1$ is also in the form of a chamfer 17. The two chamfers 16 and 17 form a symmetrical V-shaped join 18. In this embodiment the two panel surfaces S and S' are disposed in a common plane. There is therefore no heightwise displacement at the panel edges or between the panel surfaces S/S'. It will be appreciated that, instead of chamfers 16 and 17, it is also possible to provide another configuration in respect of the edge break portion, like a radius or a step, and obviously edge break portions which form a common join can also be arranged asymmetrically relative to each other or can be of differing geometrical shapes, for example an edge break portion in the form of a chamfer can be combined with an edge break portion in the form of a radius.

The tongue underside 13 has a flat lower contacting surface 13a arranged parallel to the panel surface S'. The lower groove wall 4b of the locking groove 4 has an inside 19 which is provided with a flat support surface 19a for the lower contacting surface 13a of the locking tongue 5, which support surface 19a is also arranged parallel to the panel surface S. Forces acting on the panel surface S/S' from above can be transmitted to the support surface 19a of the lower groove wall 4b by the flat contacting surface 13a of the locking tongue 5. In addition the contacting surface 13a and the support surface 19a serve for mounting and guiding the panel edges which can be in movement in the context of the existing scope for movement X and can change their relative position with respect to each other.

Figure 3B:
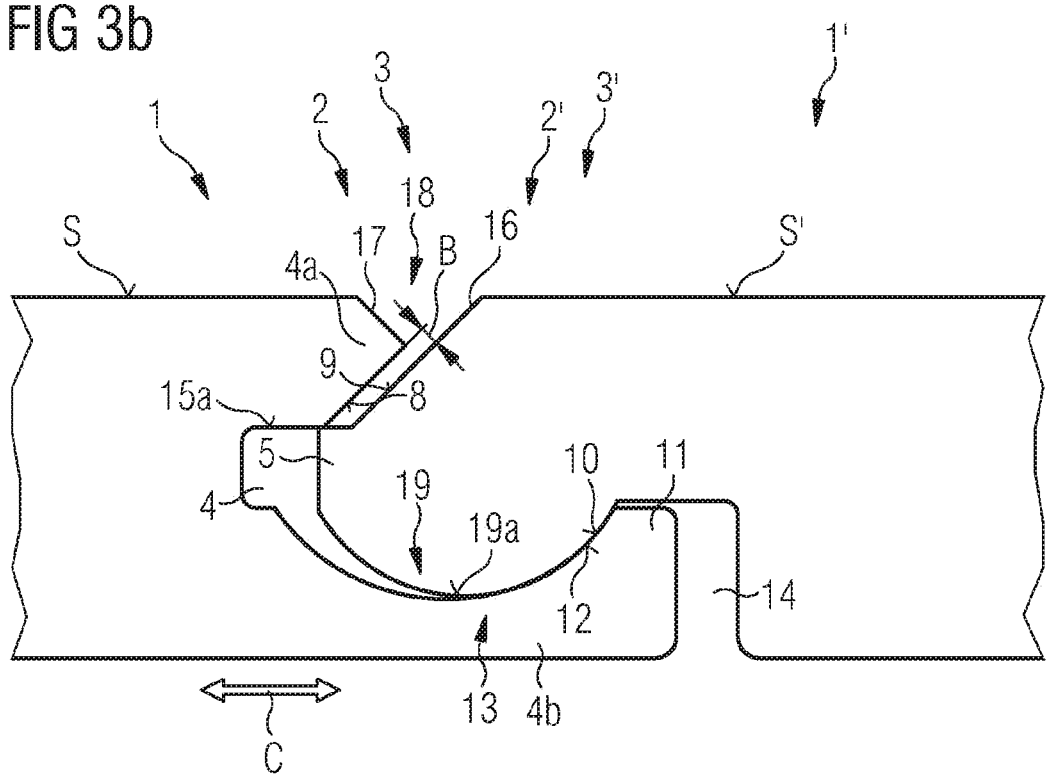
FIG. 3b shows the embodiment of FIG. 3a with mutually contacting lower contact surfaces and a gap at the butt joint which is opened to its maximum.

An alternative based on the embodiment of FIGS. 1a/1b is shown in FIGS. 2a and 2b. Reference is made to FIGS. 1a/1b. The same references are used for the same features. The alternative differs from the previous embodiment in that the two lower abutment surfaces 10 and 12 are arranged differently. The lower abutment surface 10 disposed at the holding edge 11 of the lower groove wall 4b of the locking groove 4 extends parallel to the perpendicular to the panel surface. There is no inclination relative to the perpendicular in order to avoid the effect of an inclined plane in this embodiment. In this embodiment also the lower wall of the locking groove 4 is spring-elastic and can be bent downwardly. The resilient return force can then return the lower groove wall 4b in the direction of its neutral position again. As the lower abutment surface 10 however does not form an inclined plane that return movement is not deflected into a horizontal movement of the panel edge 1' with the locking tongue 5 and the panel edges 1 and 1' are not moved towards each other. A third embodiment is shown in FIGS. 3a and 3b. This embodiment has the configuration of the edge break portions $K_1$ and $K_2$ in common with the previous embodiments and once again a portion 15a which extends horizontally in the illustrated position of use, that is to say parallel to the panel surface S', is once again disposed at the tongue top side 15 of the locking tongue 5. That portion 15a together with the locking groove 4 provides substantially for the strength of the locking connection in the vertical direction and also holds the panel surfaces S and S' in a common plane and prevents an unwanted heightwise displacement between the panel surfaces S and S'. At its tongue underside 13 the locking tongue 5 is provided with a contacting surface 13a curved upwardly with a curvature while the lower wall 4b of the locking groove 4 has at its inside 19 a support surface 19a and at its free end a holding edge 11, wherein the support surface 19a has an inwardly directed curvature which rises towards the holding edge 11 and there forms the lower abutment surface 10. The contour of the curvature of the support surface 19a is of a configuration which is wider (more open) than the contour of the curvature of the contacting surface 13a of the tongue underside 13 so that this affords a scope for movement X for the panel edges 1 and 1'. Forces acting from above on the panel 1 or 1' respectively can be diverted into the curved support surface 19a of the lower groove wall 4b by the curved contacting surface 13a of the locking tongue 5. The lower abutment surfaces 10 and 12 are a respective part of the curvature of the tongue underside 13a and the inside curvature of the lower groove wall 4b respectively. In FIG. 3b the panel edges 1 and 1' are moved away from each other. The lower abutment surfaces 10 and 12 are in contact with each other and a gap B is formed between the upper contact surfaces 8 and 9. In this embodiment, promoted by the curvature thereof, the lower groove wall 4b can be bent elastically downwardly and a return force is produced thereby, which moves the panel edges 1 and 1' towards each other again. When the lower groove wall 4b has again reached its neutral position there is nonetheless a residual gap remaining between the upper contact surfaces 8 and 9 in this embodiment.

Figure 4A:
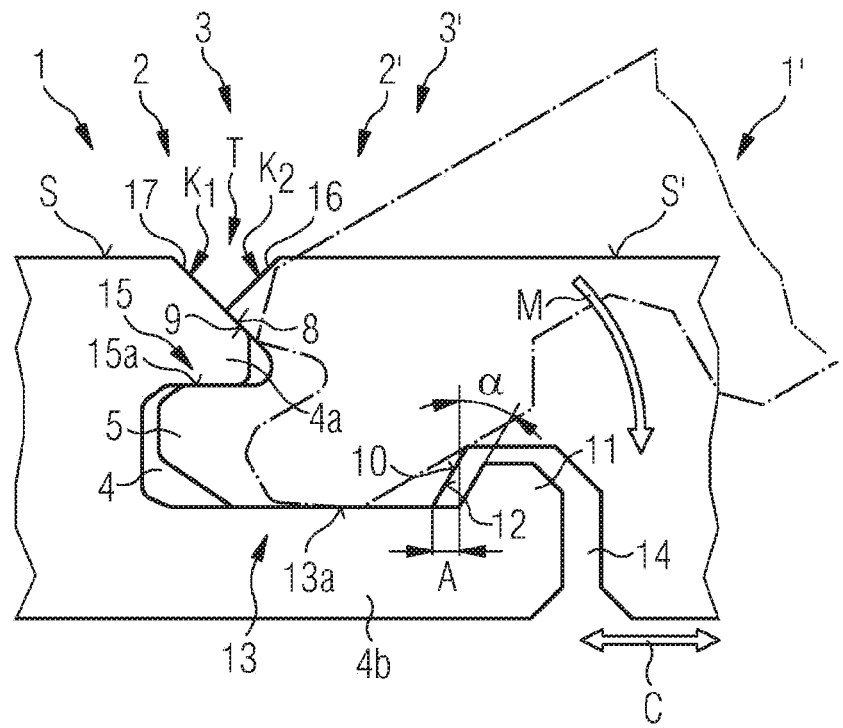
FIG. 4a shows a fourth embodiment of a panel according to the invention, wherein the panel is shown in separated relationship in order to illustrate the oppositely disposed panel edges thereof in the locked condition with the closed butt joint.
Figure 4B:
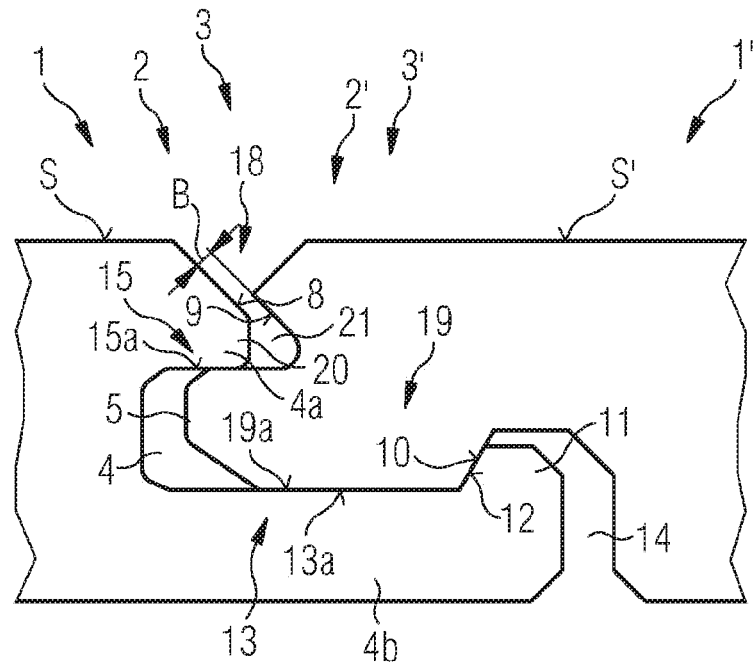
FIG. 4b shows the embodiment of FIG. 4a with mutually contacting lower contact surfaces and a gap at the butt joint which is opened to its maximum.

FIGS. 4a and 4b show a further embodiment with a locking tongue 5 and a complementary locking groove 4, wherein at its tongue top side 15 the locking tongue 5 has a portion 15a which in the illustrated position of use extends horizontally or parallel to the panel surface S/S'. Together with the complementary locking groove 4 that portion of the locking tongue 5 substantially provides for the strength of the locking connection in the vertical direction. It also holds the panel surfaces S and S' in a common plane and prevents an unwanted heightwise displacement between the panel surfaces. There are provided upper contact surfaces 8 and 9 which however are arranged at a different location from the previous embodiments. The upper contact surface 8 of that panel edge 11 which has the locking groove 4 is disposed at the outside of the free end of the upper groove wall 4a of the locking groove 4 and it is disposed in an aligned relationship or in a plane with the chamfer 17. The free end of the upper groove wall 4a acts like a tongue and fits into a groove provided for same, which is arranged at the complementary holding profile 3' above its locking tongue 5. In accordance with the invention the additional tongue is referred to as the closure tongue 20 and the additional groove is referred to as the closure groove 21 because a closed butt joint T can be produced by means of the contact surfaces 8 and 9 thereof. Consequently in this design configuration each of the holding profiles 3 and 3' has a groove and a tongue respectively, that is to say in the locked condition two grooves, namely the locking groove 4 and the closure groove 21, and two tongues, namely the locking tongue 5 and the closure tongue 20, are involved in locking of the panel edges 1 and 1'.

The embodiment of FIGS. 4a and 4b also provides that the tongue underside 14 of the locking tongue 5 has a flat contacting surface 13 arranged parallel to the panel surface S'. In this embodiment the lower groove wall 4b of the locking groove 4 is in one piece with the core of the panel and the lower groove wall 4b also has a flat support surface 19a for the lower contacting surface 13a of the locking tongue 5, which support surface 19a is arranged parallel to the panel surface S. Forces acting on the panel 1/1' from above can be diverted by the flat contacting surface 13a of the locking tongue 5 into the support surface 19a of the lower groove wall 4b. In addition the contacting surface 13a and the support surface 9 serve as mounting and guide means for the panel edges 1 and 1' which in the context of an existing scope for movement X can be in motion and can change their relative position with respect to each other. The upper contact surfaces 8 and 9 disposed on the closure tongue 20 and the closure groove 21 respectively limit the scope for movement X while the other range end of the movement is limited by the lower abutment surfaces 10 and 12 disposed on the locking tongue 5 and the locking groove 4 respectively. The edge break portions $K_1$ and $K_2$ are again in the form of chamfers 16 and 17 respectively and together form a symmetrical V-shaped join 18.

FIGS. 5a and 5b show an embodiment in which the lower abutment surfaces 10 and 12 which counteract a movement of the panel edges 1 and 1' away from each other are arranged at a different location from the preceding embodiments, more specifically at an inside 22 of the upper groove wall 4a of the locking groove 4 and at the tongue top side 15 of the locking tongue 5 respectively. The lower groove wall 4b is shorter than the upper groove wall 4a of the locking groove 4.

Figure 6A:
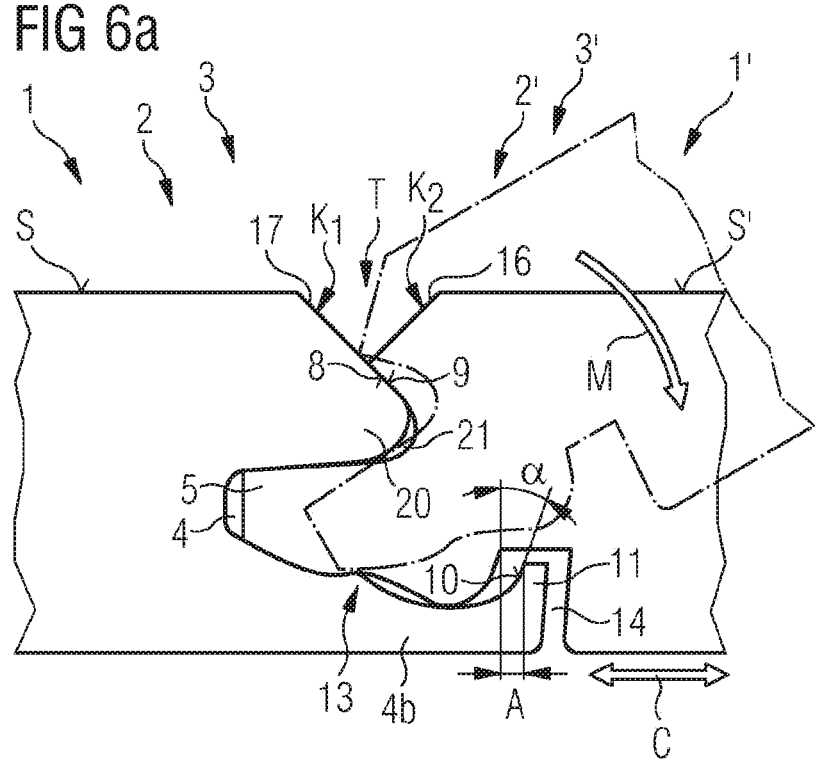
FIG. 6a shows a sixth embodiment of a panel according to the invention, wherein the panel is shown in separated relationship in order to illustrate the oppositely disposed panel edges thereof in the locked condition with the dosed butt joint.
Figure 6B:
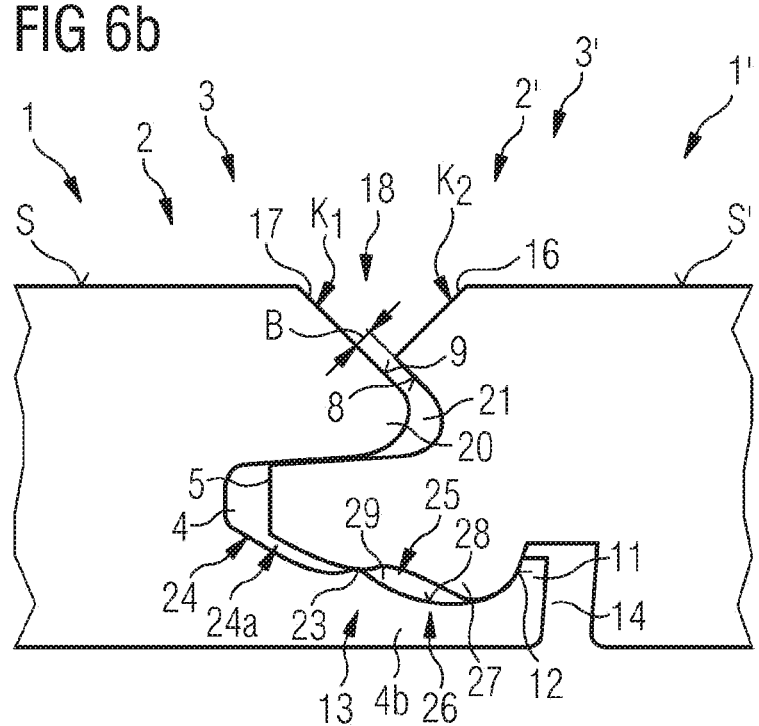
FIG. 6b shows the embodiment of FIG. 6a with mutually contacting lower contact surfaces and a gap at the butt joint which is opened to its maximum.

An alternative embodiment is shown in FIGS. 6a and 6b. This is a further embodiment in which each of the holding profiles 3 and 3' has a groove and a tongue respectively, as in the embodiment shown in FIGS. 4a/4b to which reference is directed. In other words, one of the holding profiles 3 has a locking groove 4 and at the same time a closure tongue 20, and the complementary holding profile 3' has a locking tongue 5 and at the same time a closure groove 21.

The tongue underside 13 of the locking tongue 5 has a contour with a kink 23. A front region 24 of the tongue underside 13, which is in front of the kink 23 and faces towards the tip of the locking tongue 5, has a curved contacting surface 24a which rises towards the tongue tip. In matching relationship therewith the locking groove 4 has a support surface 25 with two regions, wherein a region 25a is towards the bottom of the locking groove 4 and rises towards the groove bottom. That rising region 25a of the support surface 25 cooperates in the locked condition with the curved contacting surface 24a of the front region 24 of the tongue underside 13. A rear region 26 of the tongue underside 13 forms an outwardly curved projection 27 which projects into a recess 28 in the support surface 25 and is supported on the support surface 25. Disposed between the front curved contacting surface 24a of the tongue underside 13 and that location at which the curved projection 27 is in contact with the recess 28 is a cavity 29 in which abrasion and/or dirt particles can be accommodated.

Disposed at a rearward surface of the projection 27 is the lower abutment surface 12 of the locking tongue 5. In matching relationship therewith, provided at the free end of the lower groove wall 4b is a holding edge 11 which is directed towards the panel surface S'. The holding edge 11 has a free side which is directed towards the bottom of the locking groove 4 and at which is disposed the lower abutment surface 10 of the locking groove 4, that cooperates with the lower abutment surface 12 of the locking tongue. The lower abutment surface 10 of the locking groove 4 is arranged at an inclination through an angle α in relation to the perpendicular to the panel surface. In FIG. 6a the lower abutment surfaces 10 and 12 are at a horizontal spacing A relative to each other and the upper contact surfaces 8 and 9 are in contact with each other, as in the embodiment of FIG. 4a.

FIGS. 7a, 7b and 7c show a panel with a particularly simple construction of the panel edges 1 and 1'. It has a locking tongue 5 and a locking groove 4 as well as edge break portions $K_1$ and $K_2$ at both mutually opposite panel edges. There are upper contact surfaces 8 and 9 and lower abutment surfaces 10 and 12. In the locked condition there is a scope for movement X so that a movement of the panel edges relative to each other is possible, more specifically in a direction of movement which is both perpendicular to the positively lockingly connected panel edges and also parallel to the plane of the connected panels. The edge break portions $K_1$ and $K_2$ are each in the form of a chamfer 16 and 17 respectively. Adjoining the chamfer 16 of that panel edge 1' which has the locking tongue 5 is the upper contact surface 9. That contact surface 9 is disposed in a common plane with the chamfer 16. In this embodiment, that leads to the particularity that the upper contact surface 9 is an integral component part of the tongue top side 15 of the locking tongue 5. In addition the locking groove 4 has an upper groove wall 4a, the inside 22 of which is matched to the angle of inclination of the tongue top side 15. The inside 22 of the upper groove wall 4a thus forms the upper contact surface 8 as an integral component part of the inside 22 of the locking groove 4. The strength of the locking connection in the vertical direction is substantially afforded by the inclined tongue top side 15 together with the also inclined upper inside 22 of a locking groove 4. In addition, because of the integral structure by means of the inclined tongue top side 15 and the inside 22 of the locking groove 4 it is also possible to produce a closed butt joint T at the same time. In addition this ensures that the panel surfaces S and S' lie in one plane and that counteracts an unwanted heightwise displacement between the panel surfaces S and S'.

The lower abutment surface 10 of the panel which is provided with the locking groove 4 is disposed at the lower groove wall 4b of the locking groove 4. For that purpose the lower groove wall 4b is provided at its free end with a holding edge 11 directed upwardly relative to the panel surface S. The holding edge 11 has a free side which is directed towards the bottom of the locking groove 4 and at which the lower abutment surface 10 extends in a direction perpendicularly to the panel surface S. The lower abutment surface 12 of the panel which is provided with the locking tongue 5 is disposed at the tongue underside 13. It has an undercut 14 and thus forms a rearward side which is directed towards the core of the panel and at which the lower abutment surface 12 is formed. That lower abutment surface 12 of the locking tongue 5 extends perpendicularly to the panel surface S'.

In FIG. 7a the upper contact surfaces 8 and 9 are in contact and form a closed butt joint T. In the illustrated position of the panel edges the lower abutment surfaces 10 and 12 have a horizontal spacing A from each other, that corresponds to the scope for movement X.

FIG. 7c shows a position of the panel edges 1 and 1' in which neither the upper contact surfaces 8 and 9 touch, nor are the lower abutment surfaces 10 and 12 in contact with each other. The panel edges are locked to each other and can move relative to each other within the scope for movement X until either the range end of the scope for movement X is reached, which is defined by the contact between the upper contact surfaces 8 and 9, or they can respectively move in the opposite direction until reaching that range end of the scope for movement X, that is defined by the lower abutment surfaces 10 and 12. In the laid condition when a plurality of panels are assembled to form a floor covering a relative intermediate position will frequently occur between two locked panel edges, as indicated in FIG. 7c, in which a more or less large upper gap occurs and a more or less large space is present between the lower abutment surfaces 10 and 12 of the panel edges. During every day use the panel edges can move relative to each other and the size of the upper gap and the spacing between the lower abutment surfaces can change. An intermediate position of the panel edges relative to each other, as shown by way of example with reference to FIGS. 7c, 8c and 10c, is obviously also possible in all other embodiments, in which respect however for the sake of simplicity additional views for those embodiments have been dispensed with. In addition as shown in FIG. 7a the inside 19 of the lower groove wall 4b of the locking groove 4 has a horizontal support surface 19a which extends parallel to the panel top side S and a front region 19b which rises towards the groove bottom.

At its tongue underside 13 the locking tongue 5 has a horizontal contacting surface 13a extending parallel to the panel top side S'. In addition provided at the tongue underside 13 is a pronounced front region 13b which rises towards the tip of the locking tongue 5. In the locked condition there is no contact between the rising region 19b of the inside 19 of the lower groove wall and the rising region 13b of the tongue underside 13. Only the horizontal regions of the support surface 19a and the contacting surface 13a bear against each other.

Insofar as there is an edge break portion at the underside of a panel edge or a panel, in the previous and in the following embodiments, that preferably serves to protect the edge from damage.

Figure 8A:
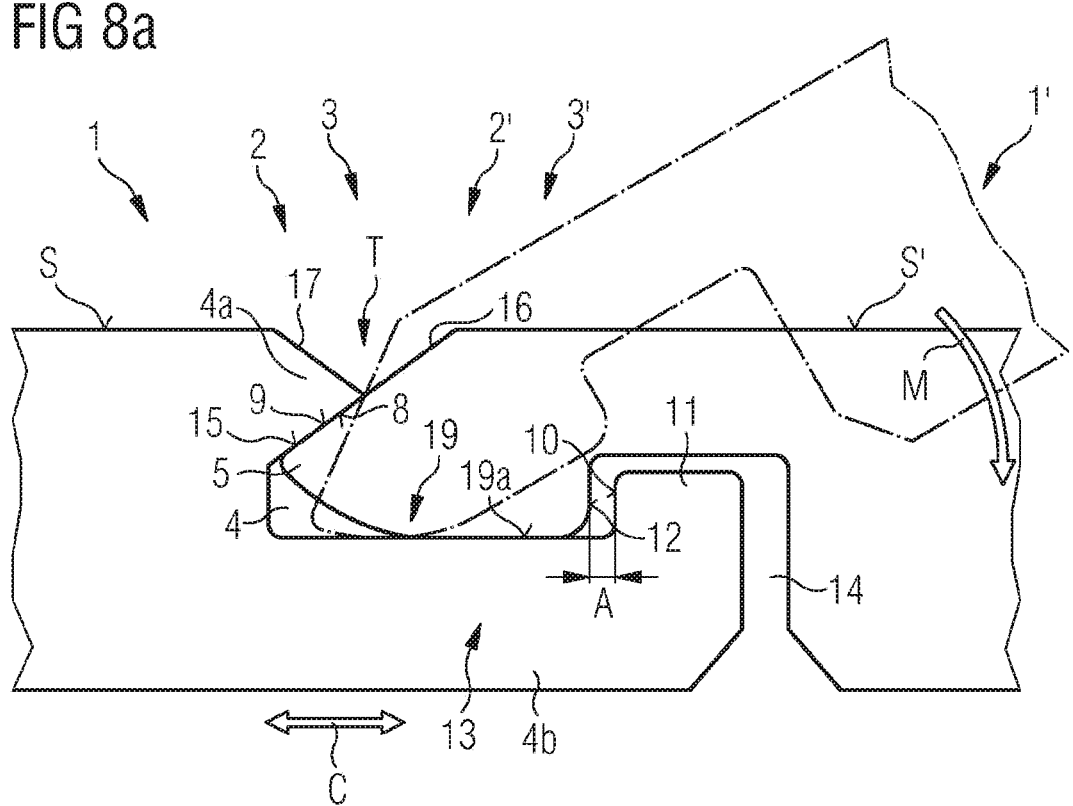
FIG. 8a shows a eighth embodiment of a panel according to the invention, wherein the panel is shown in separated relationship in order to illustrate the oppositely disposed panel edges thereof in the locked condition with the closed butt joint.
Figure 8B:
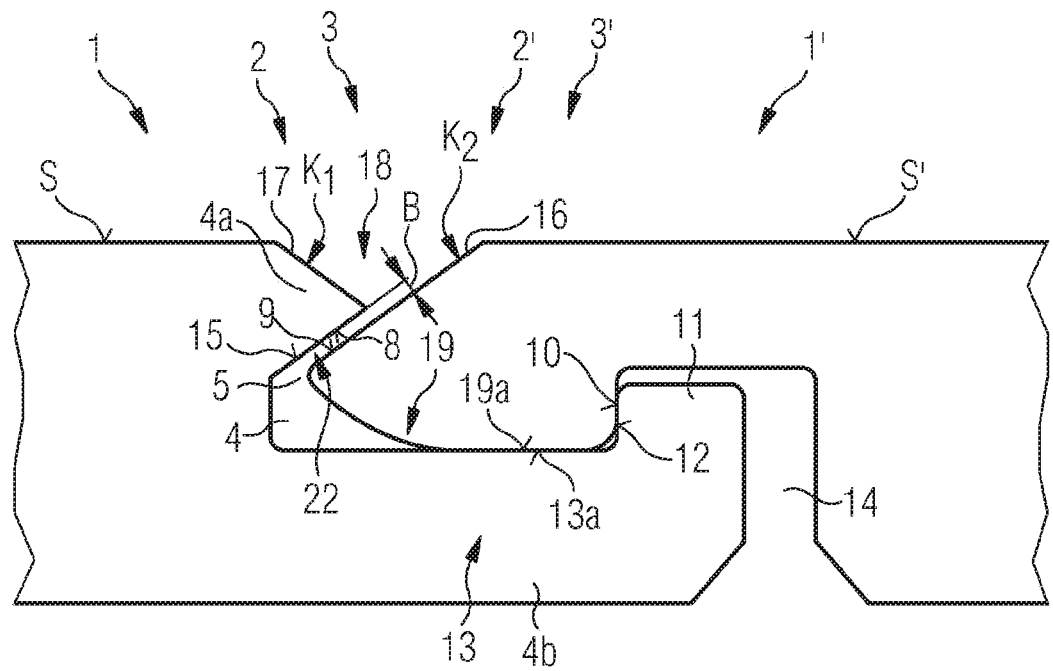
FIG. 8b shows the embodiment of FIG. 8a with mutually contacting lower contact surfaces and a gap at the butt joint which is opened to its maximum.
Figure 8C:
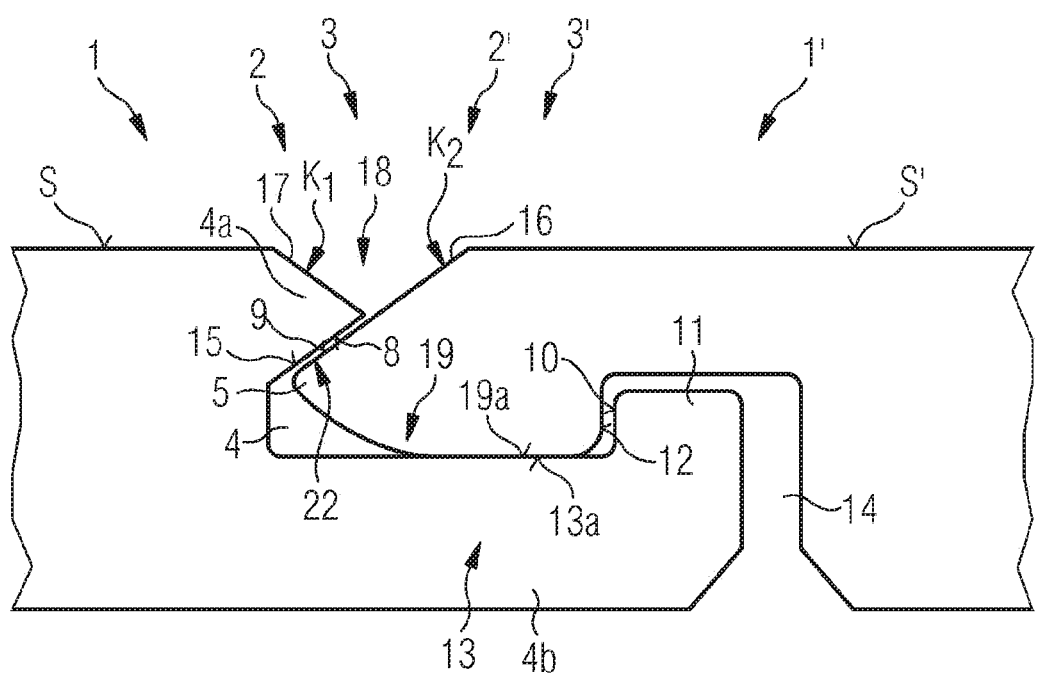
FIG. 8c shows the embodiment of FIGS. 8a/8b with lower contact surfaces at a certain spacing from each other and with a certain gap at the opened butt joint.

The embodiment of FIGS. 8a and 8b is based on the previous embodiment to which reference is directed. In comparison therewith, the configuration of the locking groove 4 has been modified. The previous embodiment has a rising region 19b at the inside 19 of the lower groove wall 4b, which region 19b extends to the bottom of the locking groove 4. Unlike that, the present embodiment dispenses with a rising region at the inside 19. As shown in FIG. 8a the inside 19 extends substantially as far as the bottom of the locking groove parallel to the panel surface (horizontally). The tongue underside 13 of the locking tongue 5 has remained the same as that in FIG. 7a, that is to say there is a rising region 13b at the tongue underside 13, towards the tip of the locking tongue 5. That modification provides that there is a larger free space than in the embodiment of FIG. 7a, between the rising region 13b of the tongue underside and the horizontal inside 19 having the support surface 19a.

FIG. 8c, like FIG. 7c, shows a position of the panel edges 1 and 1', in which neither the upper contact surfaces 8 and 9 are in contact nor are the lower abutment surfaces 10 and 12 in contact with each other. The panel edges are locked together and can move within the scope for movement X relative to each other until either the range end of the scope for movement X is reached, which is defined by the contact of the upper contact surfaces 8 and 9, or they can respectively move in the opposite direction until reaching that range end of the scope for movement, which is defined by the lower abutment surfaces 10 and 12.

Figure 9A:
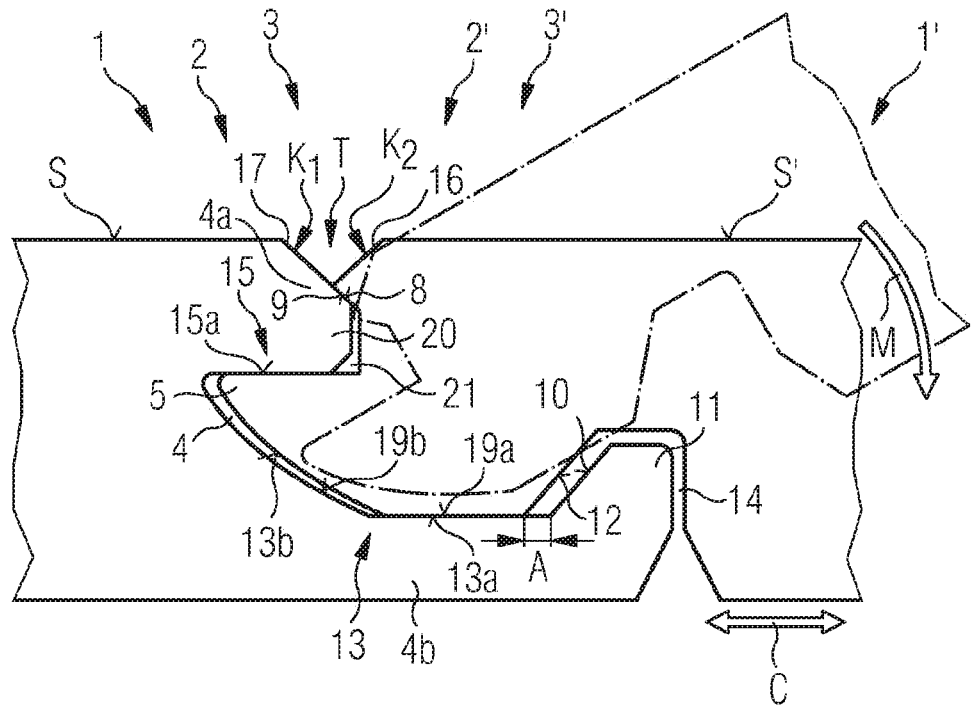
FIG. 9a shows a ninth embodiment of a panel according to the invention, wherein the panel is shown in separated relationship in order to illustrate the oppositely disposed panel edges thereof in the locked condition with the closed butt joint.
Figure 9B:
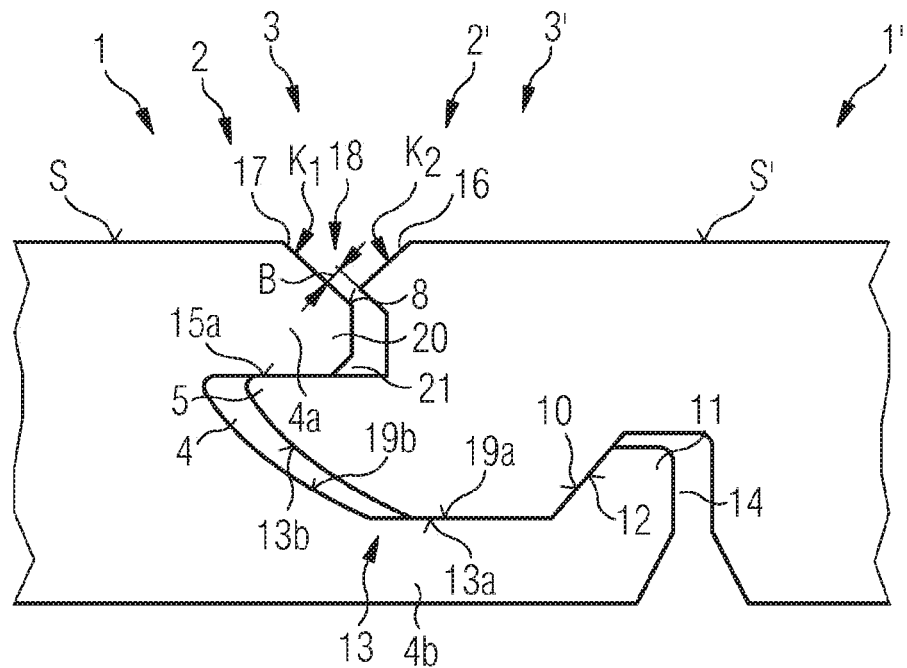
FIG. 9b shows the embodiment of FIG. 9a with mutually contacting lower contact surfaces and a gap at the butt joint which is opened to its maximum.

FIGS. 9a and 9b show a third embodiment of a panel whose complementary holding profiles 3 and 3' have a groove and a tongue respectively, as in the embodiments shown in FIGS. 4a/4b and 6a/6b, to which reference is directed. In other words, one of the holding profiles 3 has a locking groove 4 and at the same time a closure tongue 20 while the complementary holding profile 3' has a locking tongue 5 and at the same time a closure groove 21.

The panel in FIG. 9a differs from that shown in FIG. 4a substantially by a modified configuration of the locking groove 4. As shown in FIG. 9a the locking groove 4 has a lower groove wall 4b with an inside 19 which has a pronounced rising region 19b. The rising region 19b rises upwardly in the direction of the bottom of the locking groove 4. In addition the inside 19 has a support surface 19a extending parallel to the panel surface S (horizontally). The rising region 19b ends somewhat below the free end of the upper wall 4a of the locking groove 4. The tongue underside 13 has a contacting surface 13a which extends parallel to the panel surface and a front region 13b rising towards the tip of the locking tongue 5.

The lower abutment surfaces 10 and 12 are arranged inclinedly as in FIG. 4a in relation to the perpendicular to the panel surface S/S'.

This arrangement has upper contact surfaces, more specifically the upper contact surface 8 of that panel edge 1 which has the locking groove 4 is provided at the outside of the free end of the upper groove wall 4a of the locking groove 4. That free end of the upper groove wall 4a acts like a tongue and fits into a groove which is provided for same and which is arranged on the complementary holding profile 3' above its locking tongue 5. The complementary contact surface 9 is arranged in that groove on an upper groove wall. The additional tongue, in accordance with the invention, is again referred to as the closure tongue 20 and the additional groove is referred to as the closure groove 21 because they carry the contact surfaces 8 and 9 which ideally close the butt joint T.

Figure 10A:
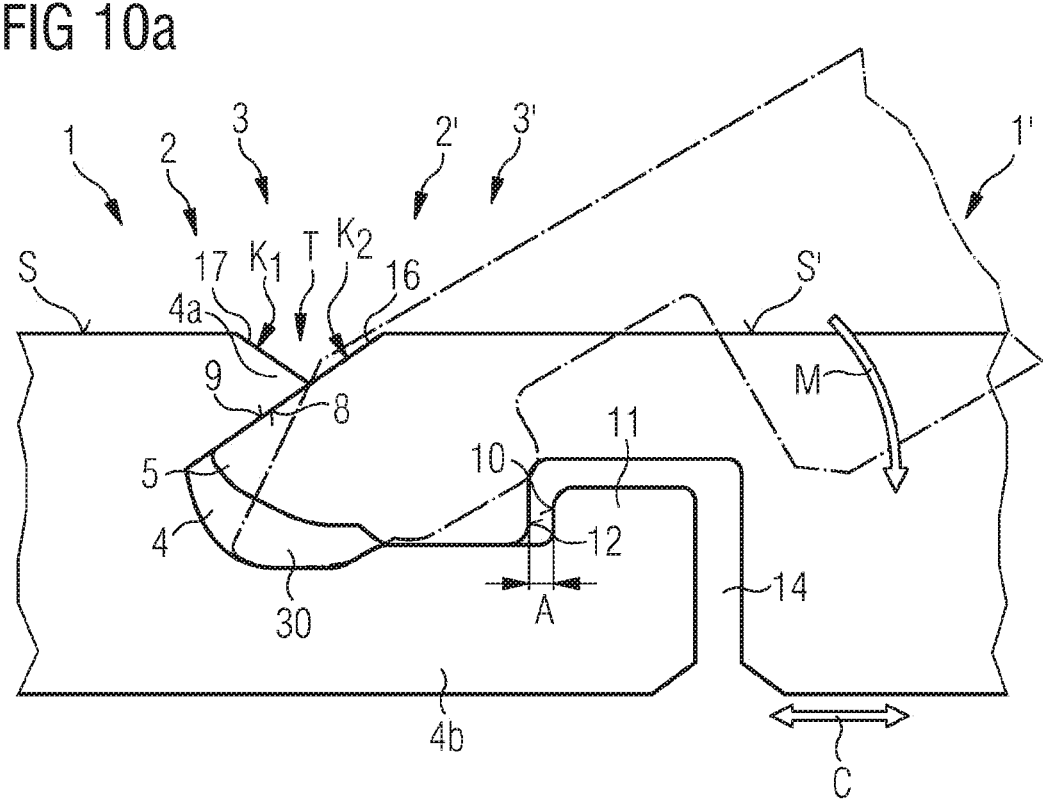
FIG. 10a shows a tenth embodiment of a panel according to the invention, wherein the panel is shown in separated relationship in order to illustrate the oppositely disposed panel edges thereof in the locked condition with the closed butt joint.
Figure 10B:
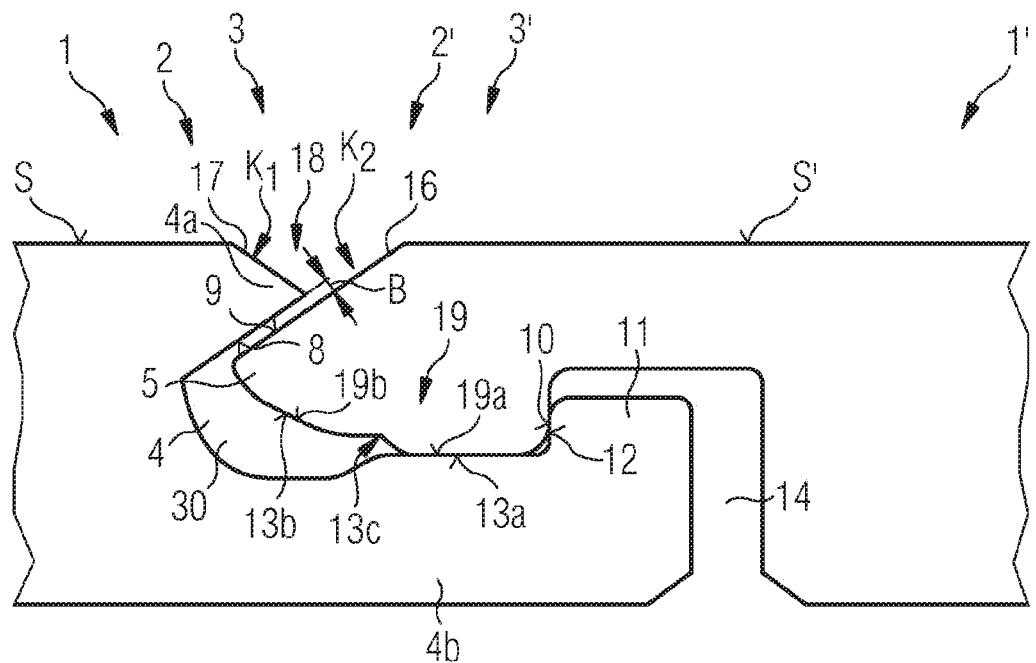
FIG. 10b shows the embodiment of FIG. 10a with mutually contacting lower contact surfaces and a gap at the butt joint which is opened to its maximum.
Figure 10C:
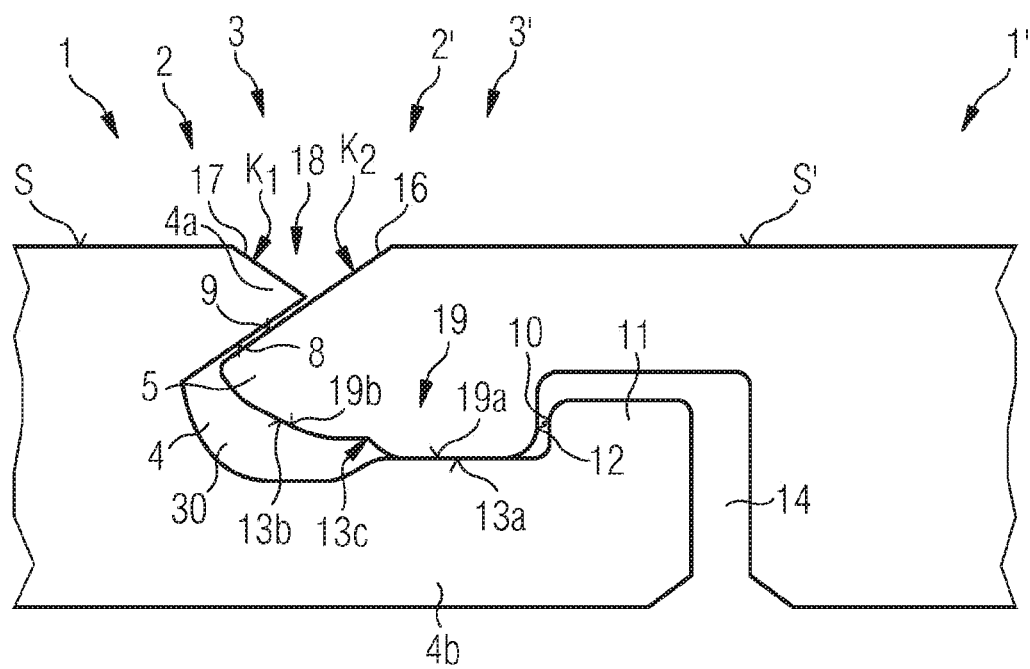
FIG. 10c shows the embodiment of FIGS. 10a/10b with lower contact surfaces at a certain spacing from each other and with a certain gap at the opened butt joint.

FIGS. 10a and 10b represent an embodiment which is based on the embodiment of FIGS. 7a/7b to which reference is directed. As a difference in relation thereto, substantially the inside 19 of the lower groove wall 4b of the locking groove 4 is modified. The inside 19 of the lower groove wall 4b has substantially two regions. A first region is formed by a support surface 19a extending parallel to the panel top side S. That support surface 19a extends as far as a lower abutment surface 10 provided on a holding edge 11 of the lower groove wall 4b. The support surface 19a extends from there in the direction of the bottom of the locking groove 4, in which respect however it does not extend as far as the bottom of the groove. Provided between the end of the support surface 19a and the groove bottom is a recess 19c which lies lower than the support surface 19a. The tongue underside 13 of the locking tongue 5 also has substantially two regions. A first region is formed by a contacting surface 13a which extends parallel to the panel top side and which cooperates with the support surface 19a of the lower groove wall 4b of the locking groove 4. A second region 13b of the tongue underside 13 faces towards the tip of the locking tongue 5. That second region has a step 13c which fits to the contacting surface 13a and which is adjoined by a curved rising region 13b which rises towards the tip of the locking tongue 5. The step 13c is set back with respect to the contacting surface 13a, that is to say its spacing relative to the panel surface S' is less than that of the contacting surface 13a. An enlarged free space 30 is afforded in the locked condition by virtue of the step 13c at the tongue underside 13 and due to the recess 19c in the lower groove wall 4b. By virtue of the free space 30 it is possible for that panel 1' to be fitted inclinedly with the locking tongue 5, as shown by means of the dash-dotted line in FIG. 10a, without the holding profiles 3 and/or 3' having to be elastically deformed.

The tip of the locking tongue 5 or its rising front region 13b can be lowered in this inclined position of the panel 1' on to the bottom of the recess 19c in the lower groove wall 4b, as indicated by the inclined panel edge indicated by a dash-dotted line.

As shown in FIGS. 10a and 10b the lower abutment surfaces 10 and 12 also extend in a direction perpendicular to the panel plane, as in FIGS. 7a/7b.

FIG. 10c shows a position of the panel edges 1 and 1' in which neither the upper contact surfaces 8 and 9 are in contact nor are the lower abutment surfaces 10 and 12 in contact with each other. The panel edges are locked to each other and can thus move relative to each other within the scope for movement X until either the end of the range of the scope for movement X is reached, as is defined by the contact between the upper contact surfaces 8 and 9, or they can respectively move in the opposite direction until that range end of the scope for movement is reached, that is defined by the lower abutment surfaces 10 and 12.

Figure 11A:
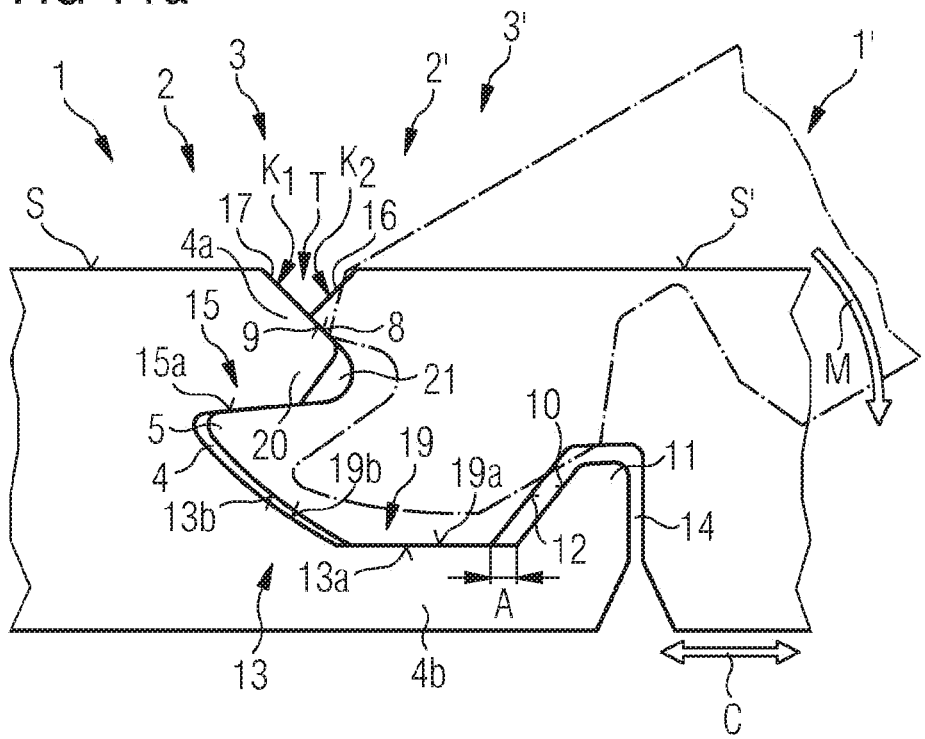
FIG. 11a shows an eleventh embodiment of a panel according to the invention, wherein the panel is shown in separated relationship in order to illustrate the oppositely disposed panel edges thereof in the locked condition with the closed butt joint.
Figure 11B:
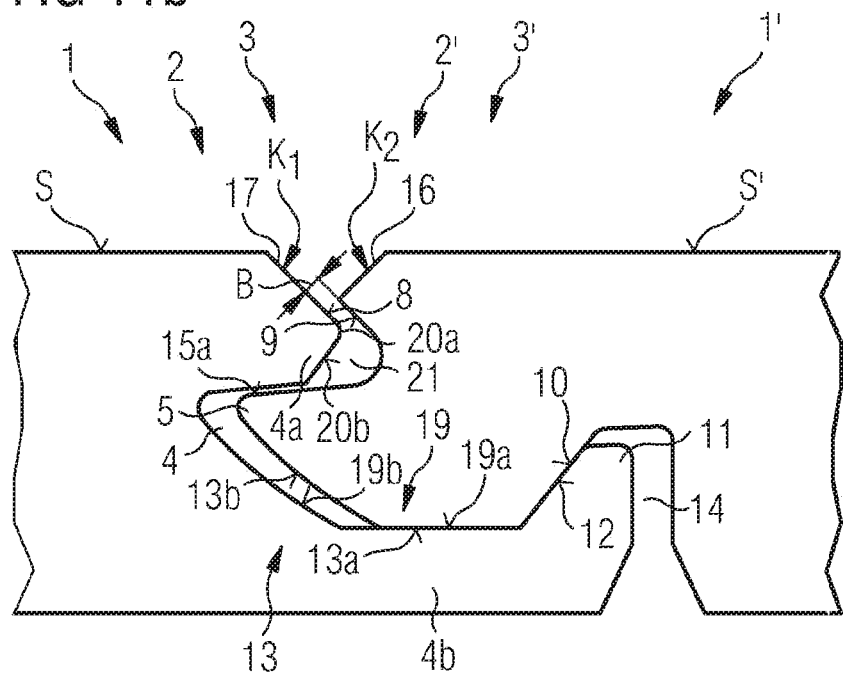
FIG. 11b shows the embodiment of FIG. 11a with mutually contacting lower contact surfaces and a gap at the butt joint which is opened to its maximum.

FIGS. 11a and 11b show an embodiment based on the embodiment of FIGS. 9a/9b, to which reference is directed. As in that case the complementary holding profiles 3 and 3' each have a groove and a tongue. In other words, one of the holding profiles 3 has a locking groove 4 and at the same time a closure tongue 20 while the complementary holding profile 3' has a locking tongue 5 and at the same time a closure groove 21.

In comparison with the embodiment shown in Figures group 9 the tongue top side 15 of the locking tongue 5 is no longer arranged parallel to the panel surface 1' but as shown in FIG. 11a it is inclined at a shallow angle with respect to the panel surface S'. The same applies to the inside 22 of the upper groove wall 4a of the locking groove 4 whose angle of inclination in the locked condition corresponds to the angle of inclination of the tongue top side 15.

The upper groove wall 4a of the locking groove 4 also forms the closure tongue 20 which in this embodiment has a tongue tip 20a and two side surfaces of which the upper side surface at the same time forms the upper contact surface 8. The lower side surface 20b is inclined relative to the panel surface S more greatly than the other part of the inside 22 of the upper groove wall 4a, the angle of inclination of which corresponds to that of the tongue top side 15. A free space is formed between the lower side surface 20b and the groove bottom when two panel edges 1 and 1' are fitted together, wherein the groove bottom in this case is of a round U-shaped configuration.

When, as shown in FIG. 11b, two locked panel edges 1 and 1' assume a position in which there is a gap between the upper contact surfaces 8 and 9 then there is also a minimal gap between the shallowly inclined tongue top side 15 and the inside 22 of the upper groove wall 4a of the locking groove 4.

Figure groups 12 through 15 show four different embodiments which involve an identical basic concept and which differ only by the configuration in the region of the edge break portion $K_1$ and $K_2$ at the panel surface S and S' respectively and by the configuration of the upper contact surfaces 8 and 9. The basic concept respectively provides a holding profile 3 having a locking groove 4 and a complementary holding profile 3' provided with a locking tongue 5 at the oppositely disposed panel edge 1'. The locking groove 4 and the locking tongue 5 always lock the panel edges 1 and 1' in positively locking relationship, more specifically on the one hand in a direction perpendicular to the panel plane and on the other hand in a direction which is perpendicular to the locked panel edges 1/1' and at the same time parallel to the panel plane (horizontally).

The locking groove 4 has an upper groove wall 4a and a lower groove wall 4b which is longer than the upper groove wall. At its free end the lower groove wall 4b has a holding edge 11 which extends upwardly in the direction of the panel surface S.

Lower abutment surfaces are provided for horizontal locking, more specifically a lower abutment surface 10 at the holding edge 11 of the lower groove wall 4b of the locking groove 4 and a lower abutment surface 12 at the tongue underside 13 of the locking tongue 5. For that purpose provided at the tongue underside 13 is an undercut 14 which has a rearward side which is directed towards the core of the panel and at which is disposed the lower abutment surface 12 of the locking tongue 5.

Both the lower abutment surface 12 of the locking tongue 5 and also the lower abutment surface 10 of the locking groove 4 extend in the examples shown in Figure groups 12 through 15 perpendicularly to the panel surface S and S'.

In Figure groups 12 through 15 the tongue underside 13 always has a flat contacting surface 13a which extends parallel to the panel surface S' and the lower groove wall 4b has an inside 19 having a support surface 19a also extending parallel to the panel surface S'. Adjoining the two ends of that contacting surface 13a are respective rising regions of the tongue underside 13. A front rising region 13b rises to the free end of the locking tongue 5. A rear region 13d rises to the lower abutment surface 12 of the locking tongue 5. The rear region 13d can be moved (pivoted) on a curve past the holding edge 11 of the lower groove wall 4b of the locking groove 4 without exerting a pressure against the holding edge 11. In that way the panel edges 1 and 1' can be very easily assembled or separated from each other, without the holding profiles 3 and 3' having to be elastically deformed. For that purpose it is sufficient for the panel with the locking tongue 5 to be pivoted upwardly, more specifically about the intersection point Z at the tip of the V-shaped join. Ideally for that reason the contour of the rear rising region 13b of the tongue underside is on a radius R whose center point is the intersection point Z of the V-shaped join.

If however a certain degree of elastic deformation of the holding profiles is wanted then somewhat more material can simply be left at the rear region 13b of the tongue underside 13 so that the contour of the rear rising region 13b then lies on a larger radius. In order then to insert the locking tongue 5 into the locking groove 4 a force has to be exerted to a certain degree on the holding edge 11 of the lower groove wall 4b so that it at least temporarily bends elastically downwardly and then entirely or partially returns in the direction of its neutral position again.

A front rising region 13b of the tongue underside 13 makes it easier for the locking tongue 5 to be inserted into the locking groove 4 by a pivotal movement M or to be pivoted out of same without exerting a substantial pressure on the lower groove wall 4b with the tongue underside 13.

Figure 12A:
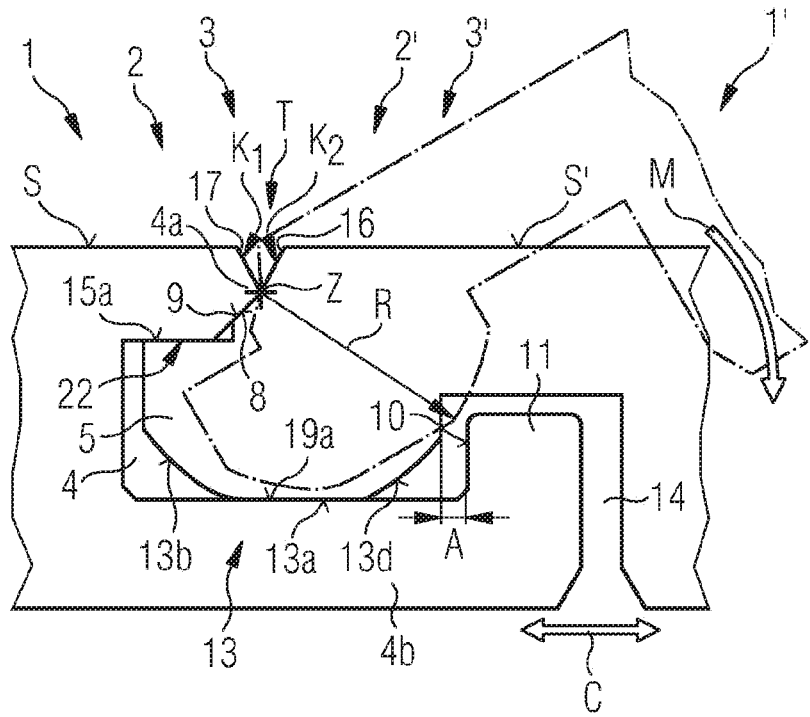
FIG. 12a shows a twelfth embodiment of a panel according to the invention, wherein the panel is shown in separated relationship in order to illustrate the oppositely disposed panel edges thereof in the locked condition with the dosed butt joint.
Figure 12B:
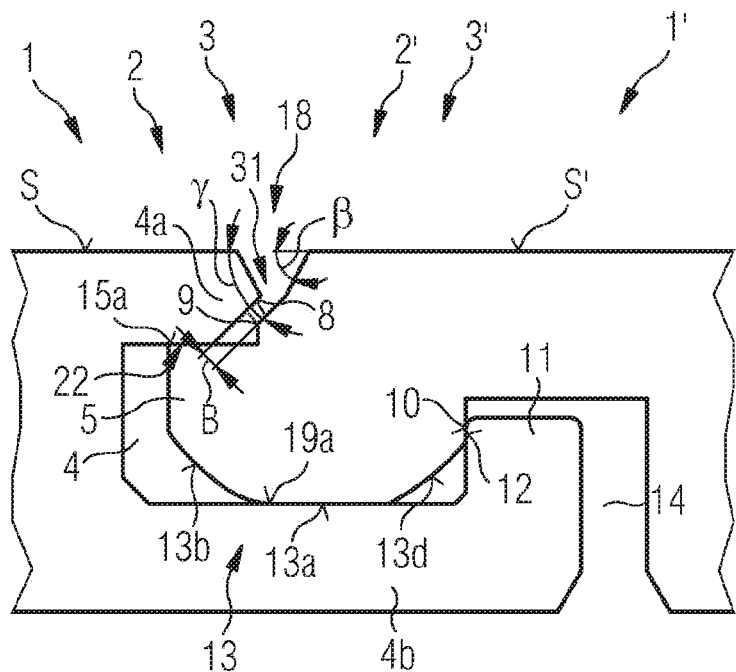
FIG. 12b shows the embodiment of FIG. 12a with mutually contacting lower contact surfaces and a gap at the butt joint which is opened to its maximum.

In FIG. 12b and in the views identified by "b" in the following groups of Figures, each Figure shows a position of the panels in which the lower abutment surfaces 10 and 12 are in contact.

In addition there are provided upper contact surfaces 8 and 9 which are in contact with each other when the panel edges 1 and 1' are moved towards each other until finally a maximum spacing is formed between the lower abutment surfaces 10 and 12, as shown in FIG. 12a. The upper contact surfaces 8 and 9 then form a closed butt joint T and the contact between the contact surfaces 8 and 9 defines a range end of a scope for movement X for the locked panel edges 1 and 1'. The other range end of the scope for movement X is defined by the contact between the lower abutment surfaces 10 and 12, as shown in FIG. 12b.

The contacting surface 13a of the tongue underside 13 and the support surface 19a of the lower groove wall 4b of the locking groove 4 serve as mounting and sliding surfaces for the relative movement of the panel edges 1 and 1' within the predetermined scope for movement X.

As mentioned the embodiments shown in Figures groups 12 through 15 differ in regard to the configuration of the edge break portion and the upper contact surfaces.

As shown in Figures groups 12 through 15 the edge break portion is in each case in the form of a chamfer. In the locked condition the chamfers 16 and 17 form a V-shaped join 18. Disposed beneath the V-shaped join are the respective upper contact surfaces 8 and 9 which are arranged parallel to each other and which can contact each other, as shown in FIGS. 12a, 13a, 14a and 15a.

In FIG. 12a the chamfer 16 of that panel edge 1' which has the locking tongue 5 is inclined with respect to the panel surface S' through an angle β of about 60° while the upper contact surface 9 of this panel edge is inclined through a smaller angle γ of about 45° with respect to the panel surface S'. Because of the differing inclinations there is a slight kink 31 between the chamfer 16 and the upper contact surface 9. On the complementary holding profile 3 with the locking groove 4 the upper contact surface 8 is so inclined that in the locked condition of two panel edges it extends parallel to the oppositely disposed upper contact surface 9. The upper contact surface 9 extends with that inclination as far as the inside 22 of the upper groove wall 4a which is parallel to the panel surface S.

In addition FIG. 12a shows the panel edges 1 and 1' in a position in which they are butted against each other so that the upper contact surfaces 8 and 9 are in contact with each other. At the same time the lower abutment surfaces 10 and 12 are at a maximum spacing A relative to each other in that position. In FIG. 12b the panel edges 1 and 1' are so moved away from each other that a maximum gap B is formed between the upper contact surfaces 8 and 9. As a result the lower abutment surfaces 10 and 12 have at the same time come into contact with each other. As can be seen the maximum spacing A possible between the lower abutment surfaces is always greater than the maximum width of the gap B between the upper contact surfaces 8 and 9.

Because of the inclined arrangement of the upper contact surfaces 8 and 9 dirt which passes into the V-shaped join disposed thereabove, by virtue of the narrowness of the gap B, can only penetrate thereinto with greater difficulty.

In addition the inclined arrangement of the upper contact surfaces 8 and 9 prevents being able to look deeply into the gap B. A person viewing it can only see at all one of the two upper contact surfaces 9 in respect of a small part thereof because the other contact surface 8 is always concealed for a viewing person. The depth of view however remains small at the visible part of the contact surface 9.

Figure 13A:
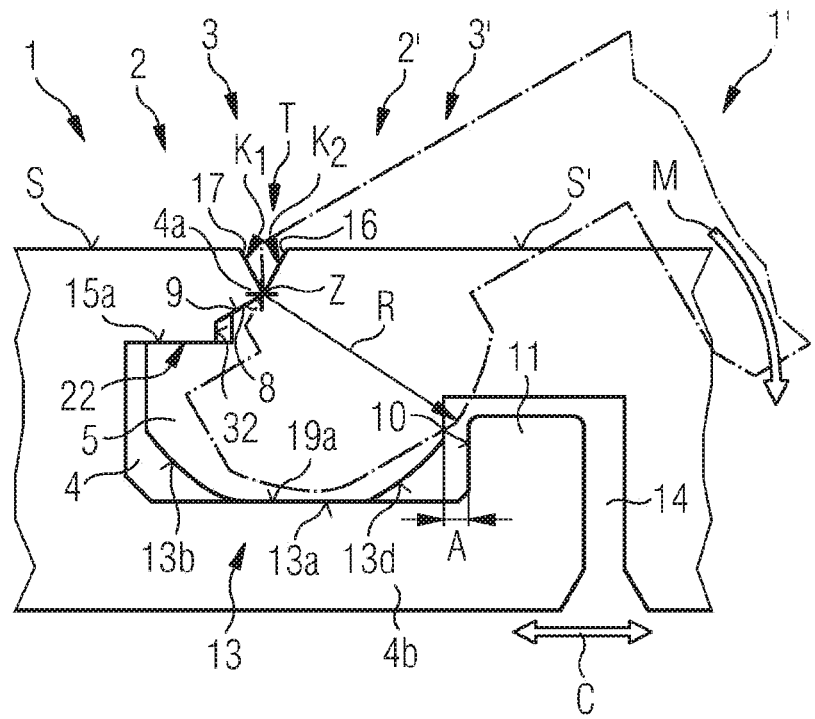
FIG. 13a shows a thirteenth embodiment of a panel according to the invention, wherein the panel is shown in separated relationship in order to illustrate the oppositely disposed panel edges thereof in the locked condition with the dosed butt joint.
Figure 13B:
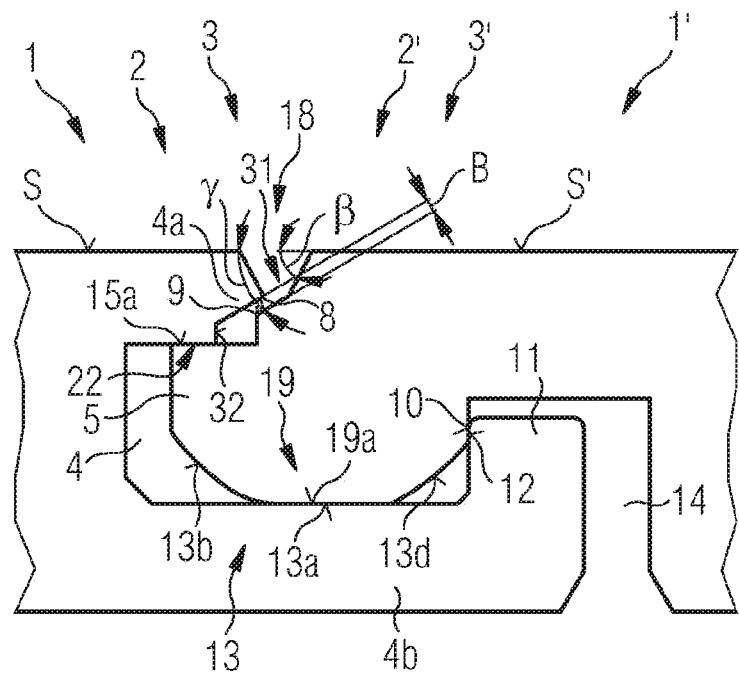
FIG. 13b shows the embodiment of FIG. 13a with mutually contacting lower contact surfaces and a gap at the butt joint which is opened to its maximum.

In the embodiment of FIGS. 13a and 13b the chamfer 16 of that panel edge which has the locking tongue 5 involves the same angle of inclination β as in FIG. 12a. The upper contact surfaces 8 and 9 however are inclined through an angle γ with respect to the panel surface S/S', which is still somewhat smaller than the angle γ in FIG. 12a. That means that the width of the gap B is narrower than in the previous embodiment. Extending between the upper contact surfaces 8 and 9 and that region of the inside 22 of the upper groove wall 4a, that is parallel to the panel surface S, there is a short portion which is perpendicular to the panel surface S so that a small step 32 is formed. If the step 32 were not present and the upper contact surface 8 extended with an angle of inclination that remained the same as far as the inside 22 of the upper groove wall 4a then the surface contact between the horizontal tongue top side 15a and the horizontal region of the upper groove wall 4a would be markedly reduced. Therefore the step 32 serves to increase the horizontal surface contact at that location and in that way to improve the strength of the locking action.

The spacing A shown in FIG. 13a between the lower abutment surfaces 10 and 12 is identical to FIG. 12a. The gap B shown in FIG. 13b however is narrower than in FIG. 12b because the upper contact surfaces 8 and 9 are arranged with a smaller angle of inclination relative to the panel surface S, than in FIG. 12b.

Figure 14A:
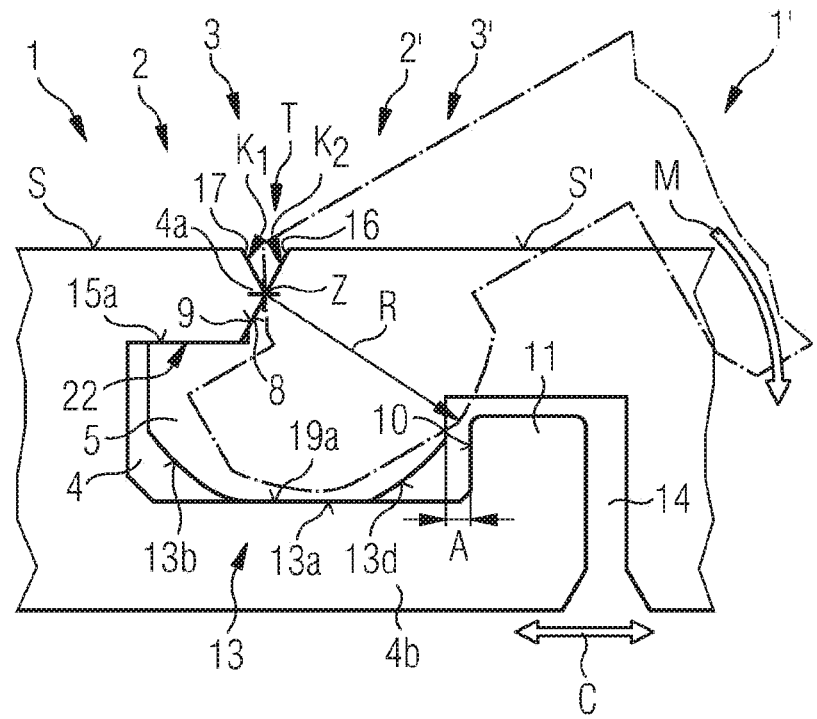
FIG. 14a shows a fourteenth embodiment of a panel according to the invention, wherein the panel is shown in separated relationship in order to illustrate the oppositely disposed panel edges thereof in the locked condition with the closed butt joint.
Figure 14B:
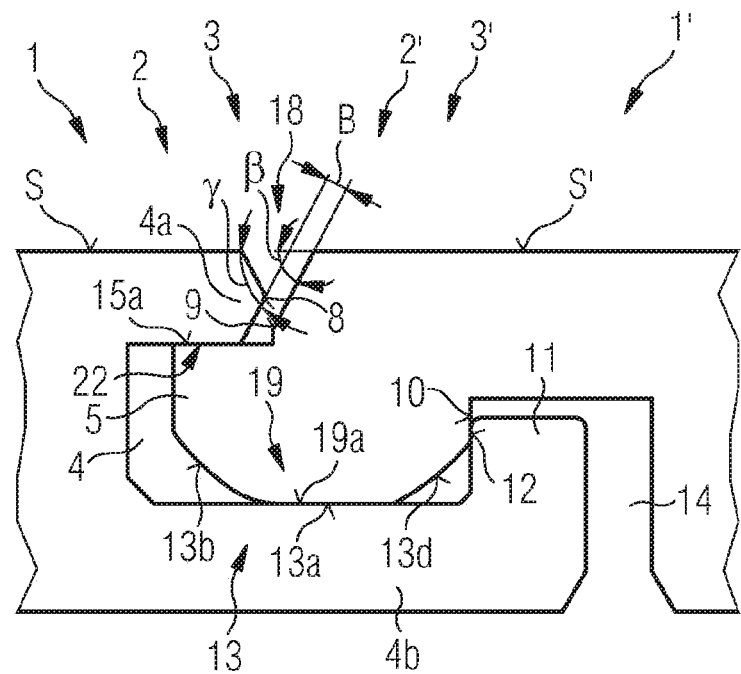
FIG. 14b shows the embodiment of FIG. 14a with mutually contacting lower contact surfaces and a gap at the butt joint which is opened to its maximum.

FIGS. 14a and 14b show an embodiment in which the chamfer 16 of that panel edge 1' which has the locking tongue 5 again involves the same angle of inclination β as in FIG. 12a. The upper contact surfaces 8 and 9 however are inclined with respect to the panel surface S/S' through an angle γ that is identical to the angle of inclination β of the chamfer 16. In other words, at that panel edge which has the locking tongue 5 the chamfer 16 and the upper contact surface 9 are arranged in a common plane. Therefore this panel edge 1' does not have a kink between the chamfer 16 and the contact surface 9.

The complementary upper contact surface 8 at the upper groove wall 4a of that panel edge with the locking groove 4 extends with an inclination that remains the same to the horizontal inside 22 of the upper groove wall 4a.

The spacing A shown in FIG. 14a between the lower abutment surfaces 10 and 12 is identical to FIG. 12a. The gap B shown in FIG. 14b however is of a greater width than in FIG. 12b because the upper contact surfaces 8 and 9 are arranged with a greater angle of inclination relative to the panel surface S than in FIG. 12b.

Figure 15A:
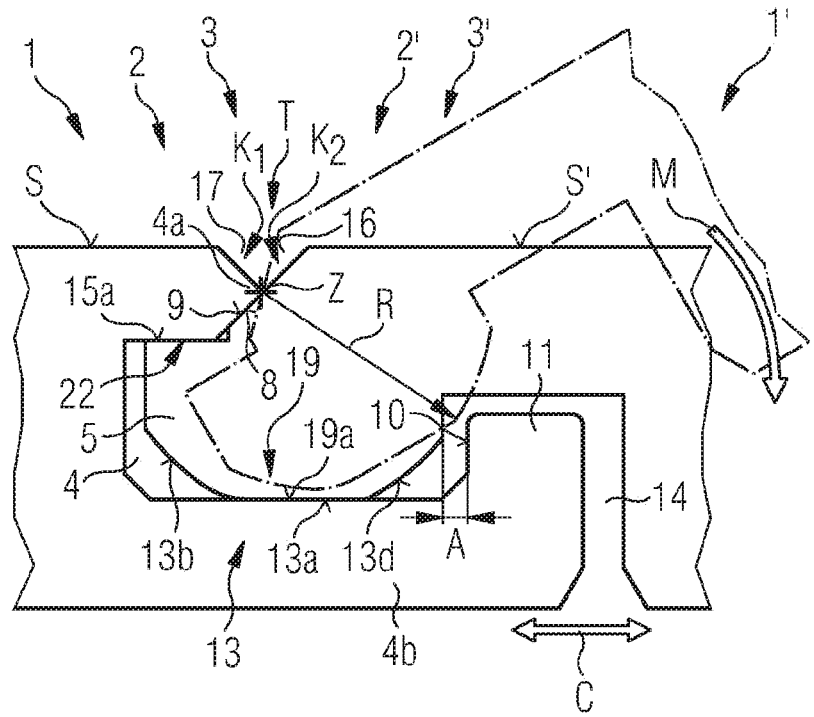
FIG. 15a shows a fifteenth embodiment of a panel according to the invention, wherein the panel is shown in separated relationship in order to illustrate the oppositely disposed panel edges thereof in the locked condition with the closed butt joint.
Figure 15B:
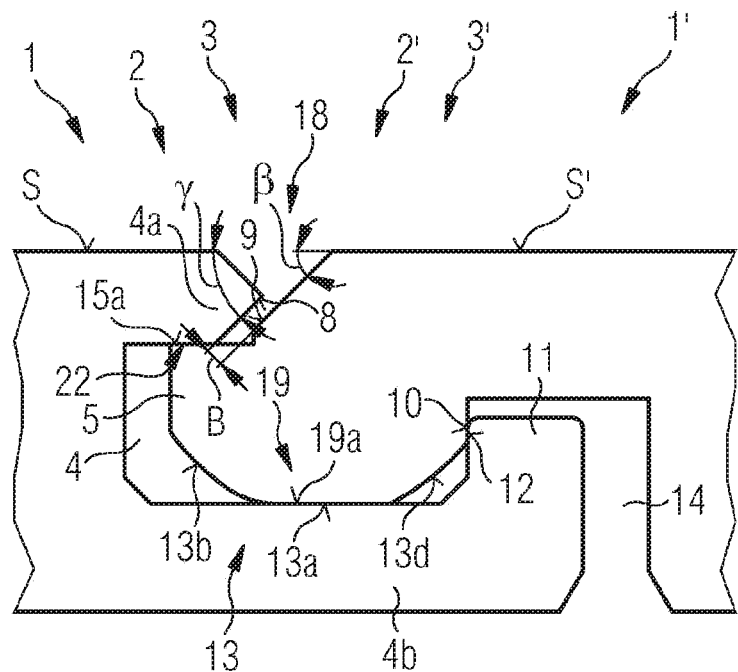
FIG. 15b shows the embodiment of FIG. 15a with mutually contacting lower contact surfaces and a gap at the butt joint which is opened to its maximum.

The embodiment of FIGS. 15a and 15b differs from the previous embodiment 14a/14b only by virtue of the modified angle of the chamfers 16 and 17. They are inclined with respect to the panel surface S/S' at a smaller angle β which here is approximately 45°. In the case of that panel edge which has the locking tongue 5 the chamfer 16 and the upper contact surface 9 are again arranged in a common plane. This means that the upper contact surface 9 of this panel edge 1' is inclined with respect to the panel surface S' through an angle γ which is identical to the angle of inclination β of the chamfer 16.

The spacing A shown in FIG. 15a between the lower abutment surfaces 10 and 12 is again identical to FIG. 12a. The gap B shown in FIG. 15b is of the same width as the gap B in FIG. 12b because the angle of inclination γ of the upper contact surfaces 8 and 9 is identical.

The width of the gap B is thus between that in FIG. 13b which is narrower and the gap width B in FIG. 14b which is larger.

LIST OF REFERENCE 1 panel edge
1' panel edge
2 locking means
2' locking means
3 holding profile
3' holding profile
4 locking groove
4a upper groove wall
4b lower groove wall
5 locking tongue
6 panel plate
7 separate strip 8 upper contact surface (locking groove)
9 upper contact surface (locking tongue)
lower abutment surface (locking groove)
11 holding edge
12 lower abutment surface (locking tongue)
13 tongue underside
13a contacting surface
13b rising front region
13c step
13d rising rear region
14 undercut
tongue top side
15a horizontal portion
16 chamfer
17 chamfer
18 V-shaped join
19 inside (lower groove wall)
19a support surface (lower groove wall)
19b rising region
19c recess
closure tongue
20a spring tip
20b lower side surface
21 closure groove
22 inside (upper groove wall)
23 kink
24 front region (tongue underside)
24a curved contact surface
support surface (locking groove)
25a rising region
26 rear region (tongue underside)
27 curved projection
28 recess (support surface)
29 cavity
free space
31 kink
32 step
C double-headed arrow
$K_1$ edge break portion
$K_2$ edge break portion
M pivotal movement
R radius
S panel surface
S' panel surface
T butt joint
Z intersection point
α angle
β angle
γ angle

The invention claimed is:

1. A panel comprising at least one pair of complementary locking means at mutually opposite panel edges, wherein the locking means are in the form of positively locking holding profiles with a locking groove and with a complementary locking tongue respectively, wherein at least at the edge of one of the holding profiles a surface of the panel has an edge break portion, with the proviso that the holding profile which is provided with the edge break portion is provided with an upper contact surface beneath the edge break portion and the complementary holding profile is provided with a complementary upper contact surface which is arranged substantially parallel thereto, and wherein a butt joint can be produced by the two contact surfaces in contact with each other, wherein the butt joint is inclined relative to the panel surface and for that purpose one of the contact surfaces is associated with the tongue and is inclined downwardly in a direction of a free end of the tongue in question and the complementary upper contact surface is associated with the groove and is inclined downwardly in a direction of a bottom of the groove in question, wherein the complementary holding profiles are so designed that they can be positively lockingly connected by a pivotal movement, wherein a closed butt joint can be produced at the panel surface of two connected panel edges, with the proviso that a first range end of a scope for movement is defined by the two contact surfaces in contact with each other, and more specifically for a movement of the panel edges relative to each other and in a direction of movement which is both perpendicular to the positively lockingly connected panel edges and also parallel to the plane of the connected panels, wherein each of the holding profiles has a respective lower abutment surface which are then spaced from each other at the maximum when the upper contact surfaces are in contact with each other and the butt joint is closed, wherein the maximum spacing between the lower abutment surfaces measures the size of the scope for movement and wherein the lower abutment surfaces when they are in contact with each other define a second range end of the scope for movement in which second range end the butt joint is open and there is a spacing between the upper contact surfaces so that one of the upper contact surfaces is movable vertically relative to the other upper contact surface, wherein the locking groove has a horizontal support surface and a region that rises nonperpendicularly from the horizontal support surface to the upper contact surface of the locking groove and a curved transition joins the upper contact surface of the locking groove to the region that rises.

2. The panel according to claim 1, wherein the edge break portion is in the form of a chamfer, the chamfer is inclined downwardly towards the free end of the locking tongue and the upper contact surface of said holding profile is also inclined downwardly towards the free end of the locking tongue, wherein an angle of inclination of the upper contact surface is less than or equal to an angle of inclination of the chamfer.

3. The panel according to claim 1, wherein a tongue top side of the locking tongue is inclined in relation to the panel surface and the tongue top side and the upper contact surface are integrated to constitute a common surface, that the locking groove at the inside of its upper groove wall is also inclined in relation to the panel surface and that the inclination thereof is matched to the inclination of the upper contact surface of the locking tongue.

4. The panel according to claim 1, wherein the locking groove has a lower groove wall with a free end at which there is provided a holding edge directed towards the panel surface, the lower abutment surface of the locking groove is arranged at the holding edge of the lower groove wall and the lower abutment surface faces inwardly towards the bottom of the locking groove.

5. The panel according to claim 1, wherein of the lower abutment surfaces at least the lower abutment surface of the locking groove is arranged perpendicularly in relation to the panel surface.

6. The panel according to claim 1, wherein a tongue underside of the locking tongue has a lower contacting surface and a lower groove wall of the locking groove is provided with a support surface for the lower contacting surface of the locking tongue, wherein the lower contacting surface of the locking tongue is arranged parallel to the panel surface and the support surface also extends parallel to the panel surface.

7. The panel according to claim 6, wherein the tongue underside of the locking tongue has a rising region at least at one end of the lower contacting surface.

8. The panel according to claim 1, wherein the holding profile with the locking tongue has a closure groove above the locking tongue and the complementary holding profile with the locking groove with its free end of the upper groove wall forms a closure tongue which can be inserted into the closure groove.

9. The panel according to claim 8, wherein the upper contact surface of that panel edge which is provided with the closure tongue is arranged at the tongue top side of the closure tongue and the upper contact surface of that panel edge which is provided with the closure groove is arranged at the upper groove wall of the closure groove.

10. The panel according to claim 1, wherein the edge break portion is in the form of a chamfer in the locking tongue, the chamfer is inclined downwardly towards the free end of the locking tongue and the upper contact surface of the locking tongue is also inclined downwardly towards the free end of the locking tongue, wherein an angle of inclination of the upper contact surface of the locking tongue, which upper contact surface of the locking tongue contacts the complementary upper contact surface of the locking groove of an adjacent panel, is larger than the an angle of inclination of the chamfer.

* * * * *